United States Patent [19]

Miller

[11] Patent Number: 5,101,656
[45] Date of Patent: Apr. 7, 1992

[54] METHOD AND APPARATUS FOR OXYGEN CONCENTRATION ANALYSIS

[75] Inventor: George W. Miller, San Antonio, Tex.

[73] Assignee: The United States of America as represented by the Secretary of the Air Force, Washington, D.C.

[21] Appl. No.: 544,555

[22] Filed: Jun. 27, 1990

[51] Int. Cl.$^5$ .............................................. G01N 33/00
[52] U.S. Cl. ................................. 73/23.2; 73/31.04; 204/153.22
[58] Field of Search .................. 73/19.12, 23.2, 31.07; 422/83; 55/16, 158; 210/321.8, 321.77

[56] References Cited

U.S. PATENT DOCUMENTS

| | | | |
|---|---|---|---|
| 2,671,337 | 3/1954 | Hulsberg | 73/23 |
| 3,367,850 | 2/1968 | Johnson | 204/1 |
| 3,518,982 | 7/1970 | Timmins et al. | 128/2 |
| 3,545,931 | 12/1970 | McKinley, Jr. | 23/232 |
| 3,572,994 | 3/1971 | Hochstrasser | 23/230 |
| 3,926,561 | 12/1975 | Lucero | 23/232 |
| 4,208,902 | 6/1980 | Kim et al. | 73/19 |
| 4,516,424 | 5/1985 | Rowland | 73/23.2 |
| 4,594,080 | 8/1988 | Holden et al. | 73/865.9 |
| 4,765,193 | 11/1988 | Leber et al. | 55/213 |
| 4,784,675 | 3/1989 | Miller et al. | 55/25 |
| 4,813,979 | 11/1989 | Miller et al. | 55/26 |
| 4,880,443 | 11/1989 | Miller et al. | 55/26 |

OTHER PUBLICATIONS

Analyzing Gas Mixtures with a Dual-Membrane Counterdiffusion Cell. Air Products and Chemicals, Imc. Bang Mo Kim, Journal of Membrane Science 1980.
Report Sam-TR-80-24 Aircraft Oxygen Generation by Membrane Permeation, Richard L. Johnson M. S. M.B.A. Nov. 1980.

*Primary Examiner*—Hezron E. Williams
*Assistant Examiner*—Shu-Cheng Kau
*Attorney, Agent, or Firm*—Bernard E. Franz; Donald J. Singer

[57] ABSTRACT

The oxygen concentration of a gas mixture primarily of oxygen, nitrogen, and argon is determined by measurement of the shell side flow through a hollow fiber permeable membrane module having a tube side and a shell side. A sample of the gas at a low pressure is applied via a gas regulator to the tube side. Compressed air for purge flow is supplied via a first flow controller to one end of the shell side. A small portion of the tube side flow permeates the membrane, enters the shell of the module and combines with the air purge flow. The measurement of the oxygen concentration is determined by the amount of flow exiting the shell side via a flowmeter to a vent. The amount of gas permeating the membrane is dependent on the partial pressure of oxygen on both sides of the membrane. Hence, as the tube side partial pressure increases, a greater quantity of permeated gas passes to the shell side of the membrane. The remaining tube side flow exits the module via a second floor controller to the vent. Signals from the flowmeter, a thermocouple, and a pressure sensor are applied to digital processing circuit each second. The digital processing circuit uses the shell side flow, temperature in degrees Kelvin and pressure converted to an equivalent altitude, and calculates the oxygen concentration in the sample gas by applying equations stored in the digital processing circuit.

3 Claims, 1 Drawing Sheet

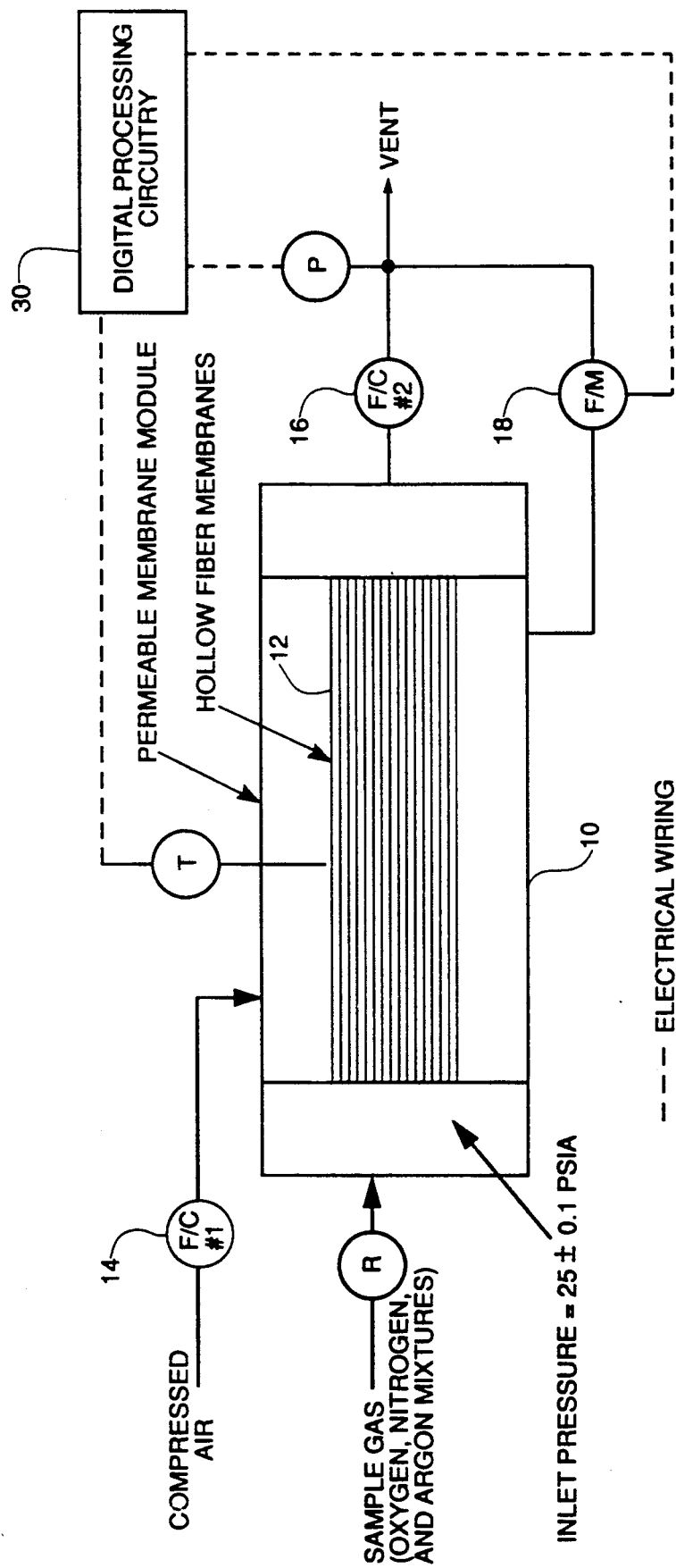

METHOD AND APPARATUS FOR OXYGEN CONCENTRATION ANALYSIS

RIGHTS OF THE GOVERNMENT

The invention described herein may be manufactured and used by or for the Government of the United States for all governmental purposes without the payment of any royalty.

BACKGROUND OF THE INVENTION

The present invention relates generally to a method and apparatus for oxygen concentration analysis.

Molecular sieve oxygen concentrators have become increasingly popular for the production of high purity oxygen (up to 95%) because of their simplicity, reduced energy consumption, and low operating costs; and in the future will replace conventional liquid oxygen converters as the primary source of breathable oxygen on-board aircraft. Also, they are used for patients requiring oxygen therapy. Molecular sieve oxygen concentrators are in use on-board military aircraft (U.S. Air Force B-1B, U.S. Navy AV-8B, and several NATO aircraft) for the production of oxygen to prevent hypoxia. These aircraft systems have become commonly known as On-Board Oxygen Generating Systems (OBOGS) or, more specifically, Molecular Sieve Oxygen Generating Systems (MSOGS). Nearly every future military aircraft will have an oxygen breathing system employing a molecular sieve oxygen concentrator.

These concentrators operate on the pressure swing adsorption technique and are capable of separating oxygen from an inlet stream of compressed air. On-board aircraft the compressed air is supplied as bleed air from the aircraft engine compressors. Using this technology, oxygen is separated from the inlet air by preferential adsorption of nitrogen within a molecular sieve. The nitrogen is vented overboard while the oxygen-rich product gas is breathed by the aircrew for the prevention of hypoxia. Use of these systems by the military has resulted in significant cost savings, enhanced aircraft versatility, and improved safety.

In their simplest form the molecular sieve oxygen concentrator is comprised of two cylindrical beds filled with a zeolite molecular sieve, several valves, and an orifice. The types of molecular sieves currently being employed are: 5AMG, MG3, 13X, and OXYSIV-5 (all manufactured by Union Carbide Corporation). The particle size of the molecular sieve pellets is generally 16×40 mesh. Typical aircraft oxygen concentrators contain approximately five to fifteen kilograms of molecular sieve depending on the amount of product flow required.

Because the oxygen concentration of the product gas is affected by the system operating conditions, such as, inlet pressure, product flow, ambient temperature, and the activity of the molecular sieve, molecular sieve oxygen concentrators generally require an oxygen concentration sensor. The sensor assures the oxygen concentrator is performing adequately for the specific application. Although several types of aircraft oxygen sensors have been proposed, such as, polarographic, fluidic, and zirconia, each has disadvantages when operating in an airborne environment.

One problem with present on-board generating systems is the lack of a reliable airborne oxygen sensor for monitoring the output of the oxygen concentrator. The sensor must have high reliability, low long-term drift, long operating life, and require little or no maintenance. Also, the sensor must be capable of performing in the aircraft environment where changes in temperature, pressure, vibration, and acceleration are always occurring. The sensor must be capable of powering up quickly and require little or no calibration except at the regular aircraft inspection intervals. Ideally, the sensor should be small in size, lightweight, inexpensive, and consume a small amount of electrical power.

The limitations and disadvantages of three types of oxygen sensors for aircraft use are listed below: (For more information on these three types, See Kocache, R. "The Measurement of Oxygen in Gas Mixtures," in "Survey of Oxygen Sensors for OBIGGS," by A. J. Meyer, Technical Operating Report #3, Appendix D, AF Aero-Propulsion Laboratory, Wright-Patterson AFB, OH (Contract F33615-84-C-2431)).

1. Polarographic oxygen sensor: This type of sensor functions by application of a voltage between a cathode and an anode which have been placed in an aqueous electrolyte such as, potassium chloride. The cathode is exposed to the sample gas which induces a redox reaction. The electrode reactions are:

$$O_2 + 2H_2O + 4e^- \rightarrow 4OH^- \text{ (cathode)}$$

$$4Ag + 4Cl^- \rightarrow 4AgCl + 4e^- \text{ (anode)}$$

Under the proper conditions the current in the cell varies linearly with the partial pressure of oxygen. The limitations and disadvantages of this type or aircraft oxygen sensor are:

a. Frequent calibration is required due to sensor drift.

b. The sensor has a limited life (generally 6 to 8 weeks).

c. The electrolyte may freeze.

2. Fluidic oxygen sensor: The fluidic oxygen sensor is dependent on the density and viscosity of the sample gas. In one configuration air is flowed into one side of a resistive bridge and the sample gas flows into the other side. The differential output pressure between the sample and reference gases is proportional to the oxygen concentration. The limitations and disadvantages of this type of aircraft oxygen sensor are:

a. Contaminants in the reference gas (bleed air), such as particulates, can clog the small passageways of the sensor These obstructions could significantly affect the sensor output.

b. The reliability of this type sensor has not been proven.

3. Zirconia oxygen sensor: This sensor is comprised of a sample chamber and reference chamber separated by a zirconium oxide disc. At high temperature the voltage between the electrodes, attached to each side of the disc, is related to the ratio of the partial pressure of oxygen at each electrode. This relationship may be expressed by the Nernst equation.

$$EMF = \frac{RT}{4F} \ln(P''_{O_2}/P'_{O_2})$$

where,

R = universal gas constant
T = absolute temperature
F = Faraday constant
P''$_{O_2}$ = partial pressure of oxygen on the reference side $P'O_2$ = partial pressure of oxygen on the sample side The limitation and disadvantages of this type of aircraft oxygen sensor are:

a. This sensor operates at a temperature of 1073 K. Operation at high temperature while exposed to high oxygen concentrations may pose a safety hazard.

b. Cycling this sensor on and off reduces sensor life.

c. This sensor requires a 10 to 20 minute warm-up time.

PATENT REFERENCES

U.S. Pat. Nos. 4,813,979 and 4,880,443 (1989) to G. W. Miller & C. F. Theis describe a secondary oxygen purifier and a molecular sieve oxygen concentrator using a combination of zeolite and carbon molecular sieve adsorption beds. U.S. Pat. No. 4,594,080, to Tremain et al describes a molecular sieve type gas separator. U.S. Pat. No. 4,765,193 to Holden et al describes an oxygen system analyzer with a commercially available polarographic sensor. U.S. Pat. No. 4,784,675 to Leber et al describes an air flow controller.

U.S. Pat. No. 4,208,902 (1980) to B. M. Kim, J. A. Quinn, and D. J. Graves titled "Gas Concentration Analysis Method and System" discloses a method and apparatus for analyzing gas concentration by measuring the steady state pressure in a dual membrane cell.

U.S. Pat. No. 3,926,561 No. (1975) to D. P. Lucero, titled "Gas Analysis Employing Semi-Permeable Membrane" covers fluid sample analysis apparatus having two fluid flow paths separated by a wall which they permeate.

U.S. Pat. No. 3,572,994 (1971) to H. Hochstrasser, titled "Analysis System for a Liquid Stream for a Gaseous Constituent" covers a system for the analysis of a stream of liquid samples for carbon dioxide content, using a sampler, proportioning pump, a gas-permeable and liquid-permeable membrane for passing carbon dioxide from the sample stream to a reagent stream, a colorimeter for examining the reagent stream and a recorder.

U.S. Pat. No. 3,545,931 (1970) to J. J. McKinley, titled "Ammonia Analysis System," discloses a system having a sample chamber and a permeation chamber separated by a membrane permeable to ammonia for decomposing ammonia into hydrogen and nitrogen, then detecting and measuring the hydrogen.

U.S. Pat. No. 3,367,850 (1968) to L. M. Johnson, titled "Method and Apparatus for Determining Moisture Content of Hydrocarbon Fluids," uses a semipermeable membrane for gas analysis.

U.S. Pat. No. 3,518,982 (1970) to R. Timmons and R. De Filippi, titled "Device and Method for Monitoring of Gases in the Blood Stream", uses a catheter having a membrane which permits diffusion of a gas being monitored.

OTHER REFERENCES

Other references of interest include the following:

1. Johnson, R. L., and S. A. Manatt, AiResearch Manufacturing Company of California, Torrance, Calif., "Aircraft Oxygen Generation by Membrane Permeation," USAF School of Aerospace Medicine Technical Report SAM-TR-80-24, Contract F33615-79-C-0609 (1980).

2. Manatt, S. A., AiResearch Manufacturing Company California, Torrance, Calif., "Design, Fabrication, and Testing of a Full-Scale Breadboard Nitrogen Generator for Fuel Tank Inerting Application," Federal Aviation Administration Technical Report FAA-RD-77-147, Contract DOT-FA75WA-3658 (1977).

3. Meyer, A. J., Boeing Military Airplane Company, Seattle, Wash., "Survey of Oxygen Sensors for OBIGGS," USAF Aero-Propulsion Laboratory, Technical Operating Report #3, Contract F33615-84-C-2431 (submitted October 1987).

4. Kim, B. M., D. J. Graves, and J. A. Quinn, "Analyzing Gas Mixtures with a Dual-Membrane Counterdiffusion Cell," *Journal of Membrane Science*, 6, 247 (1980).

SUMMARY OF THE INVENTION

An objective of the invention is to provide for the measurement of the concentration of oxygen in a gas mixture containing primarily oxygen, nitrogen, and argon. In specific, the apparatus may be useful in the measurement of the oxygen concentration in the product gas of aircraft molecular sieve oxygen concentrators (MSOCs). This measurement would assure the concentrator is producing an adequate oxygen concentration for the aircrew breathing gas. Also, this oxygen sensor could be employed to control the operation of the concentrator and/or give an alarm indication if the output oxygen concentration falls below a specified minimum concentration. Although the invention has been tested over the oxygen concentration range of 20 to 100% (the concentration range of a standard MSOGS is 21 to 95%), it is highly likely this range could be expanded to 0–100% or reduced to 0–30% with similar results.

The invention relates to a method and apparatus for measuring the oxygen concentration of a gas mixture composed primarily of oxygen, nitrogen, and argon. Oxygen concentration is determined by measurement of the shell side flow through a hollow fiber permeable membrane module. The device comprises a source of low pressure sample gas comprising primarily oxygen, nitrogen, and argon applied to a gas regulator connected to the input of the membrane module, a source of low pressure air connected to the first flow controller, a first flow controller connected to the shell side of the membrane module, a pressure sensing device connected to a digital processing circuit and a vent, a second flow controller connected between the output of the membrane module and a vent, a thermocouple connected to the membrane module and the digital processing circuit, and a flowmeter connected between the shell side of the membrane module and a vent. The measurement of the oxygen concentration of the sample gas mixture is determined by the amount of flow exiting the shell side of the membrane module. The sample gas stream enters the inlet of the pressure regulator. The purpose of the gas regulator is to maintain the module inlet pressure constant. A small portion of the flow permeates the membrane and enters the shell of the module. The amount of gas permeating the membrane is dependent on the partial pressure of oxygen on both sides of the membrane. Hence, as the tube side partial pressure increases, a greater quantity of permeated gas passes to the shell side of the membrane. The remaining tube side flow exits the module and enters the inlet of the second flow controller. Signals from the flowmeter, the temperature sensing device (i.e., the thermocouple), and the pressure sensor are applied to the digital processing circuit each second. The digital processing circuit provides data relating to shell side flow, temperature in degrees Kelvin and pressure converted to a value, A, in units Kft (thousands of feet) representing equivalent altitude. Equations stored in the digital processing circuit are used to calculate the oxygen concentration of the sample gas.

This oxygen measurement method has many advantages which may make it suitable for use in an airborne environment.

The invention may be generally applied to measure the concentration of oxygen in a gas mixture containing primarily oxygen, nitrogen, and argon. For example, the invention could be employed for the measurement of oxygen concentration in the product gas of On-board Oxygen Generating Systems (OBOGS) and Molecular Sieve Oxygen Generating Systems (MSOGS).

FEATURES

This invention employs a novel method for the measurement of oxygen concentration of gas mixtures containing primarily oxygen, nitrogen, and argon. The oxygen concentration of the sample gas is determined by measurement of the shell side gas flow of a hollow fiber membrane module. This shell side flow is a combination of the air purge flow and the membrane permeant flow.

ADVANTAGES

1. The invention appears suitable for use as an oxygen sensor for aircraft molecular sieve oxygen concentrators. Potentially, the oxygen concentration range of the invention may be expanded to 0 to 100% for use with on board inert gas generating systems or reduced to 0–30% for use in mining operations.

2. The invention has been successfully tested from an altitude of sea level to 40,000 feet.

3. The invention has been successfully tested over an ambient temperature range of 288 to 308 K. The selection of this temperature range was arbitrary. There is no reason to believe the invention would not give similar results over a wider temperature range. Ideally, if on-board an aircraft, the invention could be located in the pressurized cabin compartment. This location would permit an oxygen concentration measurement, as close as possible, to the aircrew (the inlet to the breathing regulator) and minimize the operating temperature and altitude fluctuations.

4. The apparatus contains no chemicals which require periodic replenishment.

5. The apparatus would have a long operating life. There are no chemical reactions and essentially no moving parts.

6. The apparatus consumes a small amount of electrical power.

7. The apparatus does not need to be heated, like the zirconia oxygen sensor.

8. The pressure sensing device P could be eliminated if the aircraft avionics could provide a signal representing altitude (either cabin or aircraft depending on where the exhaust gas is vented) (since altitude is defined as a function of pressure, an altitude indication is in effect an alternate form of determining the pressure at the vent).

BRIEF DESCRIPTION OF THE DRAWING

The single FIGURE is a diagram of the apparatus for oxygen concentration analysis.

DETAILED DESCRIPTION

An APPENDIX of TEST RESULTS attached hereto comprising 11 pages of text with tables and 16 sheets of drawings is hereby incorporated by reference.

The apparatus shown in the drawing provides a means for measuring the oxygen content of a gas mixture primarily containing oxygen, nitrogen, and argon. The apparatus is comprised of a permeable membrane module 10 containing hollow fiber membranes 12, two flow controllers 14 and 16 (F/C #1 and F/C #2), a flowmeter 18 (F/M), a gas pressure regulator R, a temperature sensing device T, a pressure sensing device P, and digital processing circuitry 30. The digital processing circuitry is envisioned as a separate unit.

NOTES to the Drawing

1. The flow controller 14 (F/C #1) is Tylan Corp. Model FC-260 flow controller with range of 6–300 standard cubic centimeters/minute (SCCM) or equivalent.

2. The flow controller 16 (F/C #2) is Tylan Corp. Model FC-261 flow controller with range of 0.2 to 10 standard liters/minute (SLPM) or equivalent.

3. The flowmeter 18 (F/M) is Tylan Corp. Model FM-360 flowmeter with range of 0–1000 SCCM or equivalent.

4. The permeable membrane module 10 was built by Dow Chemical Co. to specifications provided by AiResearch Manufacturing Co. under USAF Contract F33615-79-C-0609 (See SAM-TR-80-24).
   A. Membrane material: DX-810 poly-4-methyl-1-pentene.
   B. Nominal fiber I.D. = 30 $\mu$m.
   C. Nominal fiber wall thickness = 6 $\mu$m.
   D. Number of fibers = $5.1 \times 10^5$
   E. Nominal active permeating length = 19 cm.
   F. Nominal total fiber area = 11 m$^2$
   G. Nominal fiber bundle size: O.D. = 5 cm., length = 24 cm.
   H. Nominal module size: 11.5 cm × 11.5 cm × 34 cm.

5. T is a copper-constantan thermocouple or equivalent.

6. P is a Wallace and Tiernan 0–800 torr vacuum gauge or pressure transducer.

The permeable membrane module employed in this work was constructed by Dow Chemical Company to specifications provided by AiResearch Manufacturing Company under USAFSAM contract F33615-79-C-0609. The function of the module during the AiResearch contract was as an oxygen generator. The system configuration and operating parameters, when the module was set up as an oxygen generator, markedly differ from those for the invention. A photograph of the membrane module used in this work is shown in FIG. 10 of Technical Report SAM-TR-80-24, "Aircraft Oxygen Generation by Membrane Permeation," 1980 (This report is hereby incorporated by reference, and a copy is attached). This specific membrane module was selected for this study because it was readily available and contained hollow fiber membranes with a selectivity for oxygen. This module does not possess any unique features which would exclude other modules, containing other hollow fiber membrane materials with selectivity for oxygen, from being employed in this invention. In fact, this module would not be considered the optimum module for use with the invention. A module with a state-of-the-art hollow fiber membrane material with greater selectivity for oxygen would be smaller in size and allow a greater permeant flow. This increase in permeant flow would improve the accuracy and response time of the oxygen measurement.

The measurement of the oxygen concentration of the sample (inlet) gas is determined by the amount of flow exiting the shell side of the module. The sample gas stream containing primarily oxygen, nitrogen, and argon enters the inlet of pressure regulator R. In this work the oxygen concentration of the sample gas was varied from approximately 20 to 100%. Sample gases #1 through #4 simulated actual molecular sieve oxygen concentrator product gas compositions (Table 3 of the Appendix). The purpose of gas regulator R is to maintain the module inlet pressure constant at 25±0.1 PSIA. Hence, under the present operating conditions the gas regulator inlet pressure must be ≧25 PSIA. After the flow exits the gas regulator it passes through the tube side of the hollow fiber membranes. A small portion of the flow permeates through the membranes and enters the shell of the module. The amount of gas permeating through the membrane is dependent on the partial pressure of oxygen on both sides of the membrane. Hence, as the tube side partial pressure increases a greater quantity of permeant gas passes to the shell side of the membrane. The remaining tube side flow exits the module and enters the inlet of flow controller 16 F/C #2). Flow controller 16 was adjusted to permit 4.0 SLPM of sample gas to vent from the module.

An air purge flow of 250 SCCM flowed into the shell side of the module. The air pressure at the inlet to flow controller 14 (F/C #1) was approximately 35 PSIA. This flow combined with the permeant flow and served to lower the concentration of oxygen near the outer surface of the membrane. The shell side flow exited at the opposite end of the module as the incoming purge flow. The amount of shell side flow was measured by flowmeter 18 (F/M). After the shell side flow exited flowmeter 18 it combined with the exhaust flow and was vented. Also, other operating conditions (exhaust flow, inlet pressure, and purge flow) may be found which result in a linear output (Table 2 and FIG. 3 of the Appendix). The 0 to 5 VDC signal from flowmeter 18 represented a flow of 0 to 1000 SCCM.

Each second, signals from the flowmeter 18, the temperature sensing device T, and the pressure sensing device P are inputted to the digital processing circuitry 30. The digital processing circuitry would perform the following calculations:

1. The analog 0-5 VDC signal from flowmeter 18 is converted to a value, y, between 0 and 1000 SCCM representing the shell side flow.

2. The analog signal from the temperature sensing device T is converted to a value, T, representing temperature in degrees Kelvin.

3. The analog signal from the pressure sensing device P is converted to a value, A, in units of Kft (thousands of feet) representing equivalent altitude.

4. The slope of the apparatus operating line at the specific altitude and temperature is determined by Eqn 2.

$$S = a + bA + cA^2 + dT + eT^2 \qquad (2)$$

where,
S = slope of the operating line
A = altitude in thousands of feet (Kft)
T = temperature (K.)
The constants for an operating temperature range of 288° to 308 K. and altitude range of 0 to 40Kft are:
a = −70.531
b = −0.017487
c = 0.00026269
d = 0.51928
e = −0.00090479

5. The intercept of the apparatus operating line is determined by Eqn 3.

$$I = a + bT + cT^2 + d \, e^{(f/a)} \qquad (3)$$

where,
I = intercept of the operating line
A = altitude in thousands of feet (Kft)
T = temperature (K.)
The constants for the temperature range of 288 to 308 K. and altitude range of 0 to 40Kft are:
a = 8848.7
b = −62.079
c = 0.11386
d = −118.32
e = 2.718282
f = −0.11171

6. The oxygen concentration of the sample gas is calculated by Eqn 4.

$$x = \frac{y - I}{S} \quad (20.8 \leq x \leq 99.8) \qquad (4)$$

where,
x = oxygen concentration (%)
y = shell side flow (SCCM)
S = slope (from Eqn 2)
I = intercept (From Eqn 3)

Equations 2 and 3 were obtained by statistical analysis of the data collected over the temperature range of 288 to 308 K. and the altitude range of sea level to 40,000 feet. These equations were determined by Mr. Joe Fischer and Mr. Dan Bauer of USAFSAM/VNS by using commercially available statistical analysis software. These equations would probably fit data collected over a wider temperature range. However, new values for the constants would need to be determined. The equations were used to find the slope and intercept of the apparatus operating line.

In this work the calculations were performed by a FORTRAN Program run on a DEC 11/73 laboratory computer. In the actual application of the invention a computer would not be needed. The computer was set up to accept the 0-5VDC signal from flowmeter 18 each second. The program placed a lower limit of 20.8% and an upper limit of 99.8% on the measured oxygen concentration. The computer was not set up to accept signals from the temperature sensing device T and pressure sensing device P. Instead, temperature was monitored by a type T thermocouple and the altitude was monitored by a Wallace and Tiernan vacuum gauge. Both the temperature and altitude were held constant during each data run. (Data are presented in the Appendix in Tables 4 and 7, and FIGS. 11-15).

Characteristics of the invention are given below.
1. Sample flow = 4 SLPM
2. Air Purge flow = 250 SCCM
3. Module tube side inlet pressure = 25±0.1 PSIA
4. Tested altitude range = sea level to 40,000 feet (The selection of the altitude range was arbitrary. There is no reason to believe the invention would not give similar results over a wider range.)
5. Tested ambient temperature range = 288 to 308 K. (The selection of the temperature range was arbitrary.

There is no reason to believe the invention would not give similar results over a wider range.)

6. Maximum observed error in oxygen measurement = 4.4% (This error occurred at a temperature of 288 K. and sea level, and was largely due to the fit of Eqns 2 and 3.) (See Table 7 of the Appendix)

7. Response time to 90% of reading with a step change of 20.8% to 99.8% applied = 40 seconds 8. Oxygen measurement range = approx. 20 to 100% (There is no reason to believe the range could not be expanded to 0 to 100% or reduced to 0 to 30%.)

ALTERNATIVES: Use of a state-of-the-art hollow fiber permeable membrane material with greater selectivity for oxygen would reduce the size of the module and improve the accuracy in the oxygen measurement. The smaller module would have less void space on the shell side and this feature would improve the response time of the invention. A different module would probably require a different set of operating conditions (exhaust flow, purge flow, and inlet pressure). Also, the air purge flow would be more effective if the air had been distributed along the center of the membrane bundle.

It is understood that certain modifications to the invention as described may be made, as might occur to one with skill in the field of the invention, within the scope of the appended claims. Therefore, all embodiments contemplated hereunder which achieve the objects of the present invention have not been shown in complete detail. Other embodiments may be developed without departing from the scope of the appended claims.

APPEN___

TEST RESULTS

METHOD AND APPARATUS FOR OXYGEN CONCENTRATION ANALYSIS

The first test of the invention occurred on 6      198 . A schematic of the invention is given in Figure 1. The apparatus air purge flow, exhaust flow, and inlet pressure were controlled by flow controller F/C #1, flow controller F/C #2, and gas regulator R, respectively. The apparatus exhaust flow and sample gas (inlet) flow are nearly equal. On the first data run the operating conditions were: exhaust flow of 1 SLPM, inlet pressure of 20 PSIA, air purge flow of 171 SCCM, vent pressure of 746 Torr (an equivalent altitude of 500 feet), and ambient temperature of 297K. The ambient temperature was measured by thermocouple T. The vent pressure was measured by the pressure sensing device P. The module shell-side flow was measured by flow meter F/M. Bottled gases containing oxygen concentrations of 20.8, 52.0, 80.6, and 99.6% were sequentially permitted to flow into the apparatus until the shell-side flow stabilized. The remainder of the gas mixtures contained nitrogen. The shell-side flow was observed to vary with the inlet gas oxygen concentration over a range of 250 to 435 standard cubic centimeters/minute (SCCM). The data collected on 6      198 are given in Table 1 and Figure 2. Although this data gave somewhat nonlinear results, later tests at different operating conditions resulted in a nearly linear output.

Table 1. Data Collected on 6      8 .
(Apparatus vented to ambient pressure of 746 Torr; Ambient temperature = 297K)

| Sample Gas Oxygen Conc. (%) | Exhaust Flow (SLPM) | Inlet Pressure (PSIA) | Purge Flow (SCCM) | Shell-side Flow (SCCM) |
|---|---|---|---|---|
| 20.8 | 1.0 | 20 | 171 | 250 |
| 52.0 | 1.0 | 20 | 171 | 290 |
| 80.6 | 1.0 | 20 | 171 | 360 |
| 99.6 | 1.0 | 20 | 171 | 435 |
| 20.8 | 1.0 | 20 | 114 | 200 |
| 52.0 | 1.0 | 20 | 114 | 245 |
| 80.6 | 1.0 | 20 | 114 | 320 |
| 99.6 | 1.0 | 20 | 114 | 390 |

| | | | | |
|---|---|---|---|---|
| 20.8 | 1.0 | 20 | 53 | 150 |
| 52.0 | 1.0 | 20 | 53 | 192 |
| 80.6 | 1.0 | 20 | 53 | 265 |
| 99.6 | 1.0 | 20 | 53 | 345 |

Notes (see Figure 1):
Purge flow is controlled by flow controller F/C #1.
Exhaust flow is controlled by flow controller F/C #2.
Inlet pressure is controlled by gas regulator R.
Shell-side flow is measured by flow meter F/M.
The remainder of the inlet gas was nitrogen.

| Gas Mixture | Oxygen (%) | Nitrogen (%) | Argon (%) | Sum (%) |
|---|---|---|---|---|
| 1 (air) | 20.8 | 78.0 | 0.98 | 99.78 |
| 2 | 50.9 | 47.2 | 1.91 | 100.01 |
| 3 | 79.6 | 17.0 | 3.46 | 100.06 |
| 4 | 94.0 | 0.8 | 5.42 | 100.22 |
| 5 | 99.8 | 0.3 | 0.23 | 100.33 |

Note: Gas concentrations were determined by a Perkin-Elmer MGA 1100 medical gas analyzer.

Table 4. Shell-side Flow for the Apparatus Operated at Several Simulated Altitudes and Ambient Temperatures. (Exhaust flow = 4.0 SLPM; Inlet pressure = 25 PSIA; Purge flow = 250 SCCM)

| | 288K | | 298K | | 308K | |
|---|---|---|---|---|---|---|
| Gas Mixture | Shell-side Flow (Run 1) (SCCM) | Shell-side Flow (Run 2) (SCCM) | Shell-side Flow (Run 1) (SCCM) | Shell-side Flow (Run 2) (SCCM) | Shell-side Flow (Run 1) (SCCM) | Shell-side Flow (Run 2) (SCCM) |
| Altitude = Sea Level; Pressure = 760 Torr | | | | | | |
| 1 | 396.48 | 396.48 | 434.08 | 434.57 | 490.23 | 490.23 |
| 2 | 487.30 | 486.33 | 528.32 | 526.37 | 580.08 | 582.03 |
| 3 | 608.40 | 605.47 | 647.46 | 642.58 | 686.52 | 690.43 |
| 4 | 675.78 | 676.76 | 710.94 | 710.94 | 746.09 | 750.98 |
| 5 | 690.43 | 693.36 | 726.56 | 727.54 | 765.63 | 768.55 |
| Altitude = 1,000 feet; Pressure = 733 Torr | | | | | | |
| 1 | 402.34 | 402.34 | 440.43 | 441.41 | 501.95 | 496.09 |
| 2 | 499.02 | 497.07 | 536.13 | 536.13 | 599.61 | 594.73 |
| 3 | 620.12 | 617.19 | 652.34 | 656.25 | 703.13 | 707.03 |
| 4 | 688.48 | 686.52 | 716.80 | 719.73 | 756.84 | 767.58 |
| 5 | 706.05 | 704.10 | 734.38 | 734.38 | 778.32 | 788.09 |
| Altitude = 2,000 feet; Pressure = 707 Torr | | | | | | |
| 1 | 412.11 | 410.16 | 450.69 | 452.15 | 509.77 | 506.84 |
| 2 | 510.74 | 505.86 | 546.88 | 547.85 | 605.47 | 606.45 |
| 3 | 629.88 | 625.00 | 662.11 | 666.99 | 709.96 | 719.73 |
| 4 | 697.27 | 697.27 | 728.52 | 734.38 | 767.58 | 777.34 |
| 5 | 716.80 | 711.91 | 745.12 | 750.00 | 782.23 | 793.95 |

Altitude = 4,000 feet; Pressure = 656 Torr

| | | | | | | |
|---|---|---|---|---|---|---|
| 1 | 424.80 | 423.83 | 468.75 | 467.77 | 529.30 | 532.23 |
| 2 | 528.32 | 522.46 | 568.36 | 567.38 | 626.95 | 627.93 |
| 3 | 645.51 | 642.58 | 683.59 | 685.55 | 731.45 | 734.38 |
| 4 | 715.82 | 709.96 | 750.00 | 750.00 | 790.04 | 792.97 |
| 5 | 731.45 | 729.49 | 767.58 | 768.55 | 804.69 | 808.59 |

Altitude = 8,000 feet; Pressure = 564 Torr

| | | | | | | |
|---|---|---|---|---|---|---|
| 1 | 452.15 | 451.17 | 496.09 | 494.14 | 559.57 | 561.52 |
| 2 | 552.73 | 552.73 | 595.70 | 594.73 | 651.37 | 655.27 |
| 3 | 669.92 | 671.88 | 708.98 | 708.98 | 754.88 | 758.79 |
| 4 | 734.38 | 741.21 | 773.44 | 773.44 | 808.59 | 813.48 |
| 5 | 751.95 | 756.84 | 791.02 | 791.99 | 825.20 | 828.13 |

Altitude = 14,000 feet; Pressure = 446 Torr

| | | | | | | |
|---|---|---|---|---|---|---|
| 1 | 473.63 | 473.63 | 518.55 | 522.46 | 580.08 | 586.91 |
| 2 | 578.13 | 576.17 | 617.19 | 622.07 | 674.80 | 678.71 |
| 3 | 690.43 | 689.45 | 728.52 | 730.47 | 770.51 | 775.39 |
| 4 | 752.93 | 753.91 | 788.09 | 789.06 | 823.24 | 828.13 |
| 5 | 769.53 | 770.51 | 805.66 | 807.62 | 842.77 | 845.70 |

Altitude = 20,000 feet; Pressure = 349 Torr

| | | | | | | |
|---|---|---|---|---|---|---|
| 1 | 484.38 | 484.38 | 530.27 | 533.20 | 593.75 | 595.70 |
| 2 | 583.98 | 583.01 | 626.95 | 629.88 | 682.62 | 683.59 |
| 3 | 695.31 | 695.36 | 733.40 | 733.40 | 777.34 | 783.20 |
| 4 | 755.86 | 756.84 | 792.97 | 793.95 | 828.13 | 834.96 |
| 5 | 772.46 | 774.41 | 807.62 | 811.52 | 847.66 | 851.56 |

Altitude = 30,000 feet; Pressure = 226 Torr

| | | | | | | |
|---|---|---|---|---|---|---|
| 1 | 490.23 | 488.28 | 536.13 | 537.11 | 596.68 | 597.66 |
| 2 | 586.91 | 584.96 | 629.88 | 630.86 | 687.50 | 687.50 |
| 3 | 699.22 | 695.31 | 735.35 | 738.28 | 783.20 | 783.20 |
| 4 | 760.74 | 761.72 | 799.80 | 798.83 | 833.01 | 833.98 |
| 5 | 779.30 | 777.34 | 814.45 | 815.43 | 850.59 | 853.52 |

Altitude = 40,000 feet; Pressure = 141 Torr

| | | | | | | |
|---|---|---|---|---|---|---|
| 1 | 491.21 | 489.26 | 538.09 | 538.09 | 599.61 | 605.47 |
| 2 | 587.89 | 585.94 | 628.91 | 631.84 | 689.45 | 696.29 |
| 3 | 700.20 | 699.22 | 737.30 | 739.26 | 787.11 | 792.97 |
| 4 | 763.67 | 762.70 | 796.88 | 801.76 | 836.91 | 846.68 |
| 5 | 778.32 | 777.34 | 813.48 | 817.38 | 854.49 | 866.21 |

Notes (see Figure 1):
Purge flow is controlled by flow controller F/C #1.
Exhaust flow is controlled by flow controller F/C #2.
Inlet pressure is controlled by gas regulator R.
Shell-side flow is measured by flow meter F/M.

Based on Figures 4-6, it appears the apparatus produces a shell-side flow which varies nearly linearly with the inlet gas oxygen concentration, regardless of vent pressure (altitude) and ambient temperature. One should also note that the apparatus has a greater shell-side flow when subjected to gas mixture #5 (99.8% oxygen, 0.23% argon, and 0.3% nitrogen) as compared to gas mixture #4 (94.0% oxygen, 5.42% argon, and 0.8% nitrogen) (Tables 3 and 4). This result suggests the apparatus is truly selective for oxygen when in the presence of argon, otherwise, the shell-side flow for both gas mixtures would have been equal. The data of Table 4 were then analyzed by a least squares technique to find the best fitting slopes and intercepts for Eqn 1 at each altitude and temperature (Table 5), $$y = Sx + I \qquad (1)$$

where,
- y = shell-side flow (SCCM)
- x = oxygen concentration of the inlet gas (%)
- S = slope
- I = intercept Table 5. Experimental Slopes and Intercepts for the Data Given in Table 4.

| Altitude (feet) | 288K Slope | 288K Intercept | 298K Slope | 298K Intercept | 308K Slope | 308K Intercept |
|---|---|---|---|---|---|---|
| 0 | 3.8442 | 306.35 | 3.7962 | 346.92 | 3.5569 | 409.58 |
| 1,000 | 3.9190 | 311.84 | 3.8020 | 354.30 | 3.6255 | 419.10 |
| 2,000 | 3.9219 | 321.01 | 3.8338 | 363.86 | 3.6031 | 429.25 |
| 4,000 | 3.9488 | 334.88 | 3.8621 | 381.19 | 3.5491 | 452.90 |
| 8,000 | 3.9093 | 363.68 | 3.8102 | 409.87 | 3.4228 | 485.44 |
| 14,000 | 3.8103 | 389.84 | 3.6705 | 439.63 | 3.3181 | 511.61 |
| 20,000 | 3.7161 | 401.91 | 3.5674 | 453.09 | 3.2565 | 523.09 |
| 30,000 | 3.7217 | 405.53 | 3.5851 | 456.17 | 3.2466 | 526.60 |
| 40,000 | 3.7204 | 406.79 | 3.5758 | 457.49 | 3.2879 | 530.59 |

The slopes and intercepts given in Table 5 are plotted in Figures 7 and 8. These experimental slopes and intercepts were correlated with temperature and altitude by Eqns 2 and 3 shown below (see Figures 7-10). These equations were obtained by Mr Joe Fischer and Mr Dan Bauer (USAFSAM/VNS) using commercially available statistical analysis software. The magnitude of the error between the experimental and calculated parameters is given in Table 6. Based on Table 6, Eqns 2 and 3 correlate the slope and intercept parameters reasonably well. The greatest error (3.6%) occurred at sea level and 288K.

Slope:
$$S = a + bA + cA^2 + dT + eT^2 \quad (T = 288 \text{ to } 308K) \quad (2)$$
$$(A = 0 \text{ to } 40 \text{ Kft})$$

where,
- S = calculated slope
- A = altitude (thousands of feet)
- T = ambient temperature (K)
- a = -70.531
- b = -0.017487
- c = 0.00026269
- d = 0.51928
- e = -0.00090479

Intercept:
$$I = a + bT + cT^2 + d\exp^{(fA)} \quad (T = 288 \text{ to } 308K) \quad (3)$$
$$(A = 0 \text{ to } 40 \text{ Kft})$$

where,
- I = calculated intercept
- A = altitude (thousands of feet)
- T = ambient temperature (K)
- a = 8848.7
- b = -62.079
- c = 0.11386
- d = -118.32
- f = -0.11171

Table 6. Error Between the Experimental Parameters Given in
Table 5 and Calculated Parameters as Determined by
Eqns 2 and 3. (Exp.= experimental;Calc.= calculated;
S = slope;I = intercept; Diff.= Calc.- Exp. )

| Altitude (ft) | Exp. S | Calc. S | Diff. S | Error (%) | Exp. I | Calc. I | Diff. I | Error (%) |
|---|---|---|---|---|---|---|---|---|
| T = 288K ||||||||
| 0 | 3.8442 | 3.9733 | +0.1291 | +3.4 | 306.35 | 295.36 | -10.99 | -3.6 |
| 1,000 | 3.9190 | 3.9561 | +0.0371 | +0.9 | 311.84 | 307.86 | -3.98 | -1.3 |
| 2,000 | 3.9219 | 3.9394 | +0.0175 | +0.4 | 321.01 | 319.05 | -1.96 | -0.6 |
| 4,000 | 3.9488 | 3.9076 | -0.0412 | -1.0 | 334.88 | 338.00 | +3.12 | +0.9 |
| 8,000 | 3.9093 | 3.8502 | -0.0591 | -1.5 | 363.68 | 365.27 | +1.59 | +0.4 |
| 14,000 | 3.8103 | 3.7800 | -0.0303 | -0.8 | 389.84 | 388.92 | -0.92 | -0.2 |
| 20,000 | 3.7161 | 3.7286 | +0.0125 | +0.3 | 401.91 | 401.01 | -0.90 | -0.2 |
| 30,000 | 3.7217 | 3.6851 | -0.0366 | -1.0 | 405.53 | 409.54 | +4.01 | +1.0 |
| 40,000 | 3.7204 | 3.6941 | -0.0263 | -0.7 | 406.79 | 412.33 | +5.54 | +1.4 |
| T = 298K ||||||||
| 0 | 3.7962 | 3.8640 | +0.0678 | +1.8 | 346.92 | 341.76 | -5.16 | -1.5 |
| 1,000 | 3.8020 | 3.8468 | +0.0448 | +1.2 | 354.30 | 354.27 | -0.03 | -0.0 |
| 2,000 | 3.8338 | 3.8301 | -0.0037 | -0.1 | 363.86 | 365.45 | +1.59 | +0.4 |
| 4,000 | 3.8621 | 3.7982 | -0.0639 | -1.7 | 381.19 | 384.40 | +3.21 | +0.8 |
| 8,000 | 3.8102 | 3.7409 | -0.0693 | -1.8 | 409.87 | 411.67 | +1.80 | +0.4 |
| 14,000 | 3.6705 | 3.6707 | +0.0002 | +0.0 | 439.63 | 435.32 | -4.31 | -1.0 |
| 20,000 | 3.5674 | 3.6193 | +0.0519 | +1.5 | 453.09 | 447.42 | -5.67 | -1.3 |
| 30,000 | 3.5851 | 3.5758 | -0.0093 | -0.3 | 456.17 | 455.94 | -0.23 | -0.1 |
| 40,000 | 3.5758 | 3.5848 | +0.0090 | +0.3 | 457.49 | 458.73 | +1.24 | +0.3 |
| T = 308K ||||||||
| 0 | 3.5569 | 3.5737 | +0.0168 | +0.5 | 409.58 | 410.94 | +1.36 | +0.3 |
| 1,000 | 3.6255 | 3.5565 | -0.0690 | -1.9 | 419.10 | 423.44 | +4.34 | +1.0 |
| 2,000 | 3.6031 | 3.5398 | -0.0633 | -1.8 | 429.25 | 434.63 | +5.38 | +1.3 |
| 4,000 | 3.5491 | 3.5080 | -0.0411 | -1.2 | 452.90 | 453.58 | +0.68 | +0.2 |
| 8,000 | 3.4228 | 3.4506 | +0.0278 | +0.8 | 485.44 | 480.85 | -4.59 | -0.9 |
| 14,000 | 3.3181 | 3.3804 | +0.0623 | +1.9 | 511.61 | 504.49 | -7.12 | -1.4 |
| 20,000 | 3.2565 | 3.3290 | +0.0725 | +2.2 | 523.09 | 516.59 | -6.50 | -1.2 |
| 30,000 | 3.2466 | 3.2855 | +0.0389 | +1.2 | 526.60 | 525.12 | -1.48 | -0.3 |
| 40,000 | 3.2879 | 3.2945 | +0.0066 | +0.2 | 530.59 | 527.90 | -2.69 | -0.5 |

Based on Eqns 2 and 3, the apparatus could be applied as an oxygen analyzer if the altitude (vent pressure), ambient temperature, and shell-side flow were known. Using Eqns 2 and 3, the slope and intercept could then be calculated to determine the operating line (Eqn 1) at the specific altitude and temperature. The oxygen concentration of the inlet gas may then be determined by rearrangement of Eqn 1, $$x = \frac{y - I}{S} \quad (20.8 \leq x \leq 99.8) \quad (4)$$

where, $x$ = oxygen concentration of the sample gas (%)
$y$ = shell-side flow (SCCM)
$S$ = slope from Eqn 2
$I$ = intercept from Eqn 3

The apparatus was operated at ambient temperatures of 308, 298, and 288K, and altitudes from sea level to 40,000 feet with the inlet gas mixtures given in Table 3. Eqns 1, 2, and 3 were applied for calculation of the oxygen concentration. The results shown in Figures 11-15. The per cent error between the actual and measured oxygen concentration for the entire data set is given in Table 7. The greatest error observed for the apparatus (4.4%) occurred at 288K and sea level with air as the sample gas. Most of the error encountered can be attributed to the fit of Eqns 2 and 3 at these conditions (Table 6).

Table 7. Per Cent Error Between the Actual and Measured Oxygen Concentrations.
(% Error = Measured %O$_2$ - Actual %O$_2$)
(Gas mixture concentrations are given in Table 3.)

| Actual Inlet Gas Oxygen Conc. (%) | 288K Error (%) (Run 1) | 288K Error (%) (Run 2) | 298K Error (%) (Run 1) | 298K Error (%) (Run 2) | 308K Error (%) (Run 1) | 308K Error (%) (Run 2) |
|---|---|---|---|---|---|---|
| *Altitude = Sea Level; Pressure = 760 Torr* ||||||| 
| 20.8 | +4.3 | +4.4 | +2.8 | +2.9 | +1.0 | +1.3 |
| 50.9 | -2.6 | -2.7 | -2.8 | -3.2 | -3.5 | -3.3 |
| 79.6 | -1.0 | -1.5 | -0.6 | -1.5 | -3.0 | -1.5 |
| 94.0 | +1.5 | +2.5 | +1.7 | +2.0 | -0.5 | +1.8 |
| 99.8 | -0.7 | 0.0 | -0.4 | 0.0 | -1.0 | 0.0 |
| *Altitude = 1,000 feet; Pressure = 733 Torr* |||||||
| 20.8 | +3.0 | +3.2 | +1.4 | +1.6 | +1.3 | 0.0 |
| 50.9 | -2.8 | -3.2 | -3.9 | -3.6 | -1.5 | -3.0 |
| 79.6 | -1.0 | -1.4 | -2.4 | -1.1 | -1.3 | +0.3 |
| 94.0 | +1.9 | +2.2 | +0.3 | +1.6 | -0.2 | +3.2 |
| 99.8 | -0.5 | 0.0 | -1.1 | -0.8 | -0.5 | -0.1 |
| *Altitude = 2,000 feet; Pressure = 707 Torr* |||||||
| 20.8 | +2.5 | +2.1 | +1.4 | +1.8 | +0.3 | 0.0 |
| 50.9 | -2.5 | -3.6 | -3.6 | -3.2 | -2.8 | -2.5 |
| 79.6 | -1.0 | -2.0 | -2.3 | -0.7 | -2.1 | +1.0 |
| 94.0 | +1.8 | +2.6 | +0.5 | +1.8 | -0.3 | +3.3 |
| 99.8 | -0.5 | 0.0 | -0.7 | -- | -1.5 | -0.2 |
| *Altitude = 4,000 feet; Pressure = 656 Torr* |||||||
| 20.8 | +1.3 | +1.1 | +1.0 | +1.0 | +0.5 | +1.7 |
| 50.9 | -2.4 | -3.9 | -2.5 | -1.0 | -1.5 | -1.3 |
| 79.6 | -1.3 | -1.5 | -1.1 | -0.3 | -0.7 | +0.6 |
| 94.0 | +2.3 | +1.8 | +2.2 | +2.7 | +1.7 | +3.3 |
| 99.8 | -0.5 | -0.2 | -0.5 | -0.1 | -0.5 | 0.0 |
| *Altitude = 8,000 feet; Pressure = 564 Torr* |||||||
| 20.8 | +1.7 | +1.3 | +1.6 | +1.0 | +1.6 | +2.6 |
| 50.9 | -2.3 | -2.5 | -2.0 | -2.3 | -1.6 | -0.3 |
| 79.6 | -0.6 | 0.0 | -0.5 | 0.0 | -0.3 | +1.2 |
| 94.0 | +1.6 | +4.3 | +2.5 | +3.2 | +0.8 | +3.0 |
| 99.8 | -0.5 | 0.0 | -0.4 | -0.2 | -0.5 | 0.0 |
| *Altitude = 14,000 feet; Pressure = 446 Torr* |||||||
| 20.8 | +1.6 | +1.5 | +1.7 | +2.7 | +1.5 | +3.6 |
| 50.9 | -1.0 | -1.7 | -1.5 | 0.0 | -0.6 | +0.4 |
| 79.6 | -0.1 | 0.0 | 0.0 | +1.0 | -1.1 | +0.5 |
| 94.0 | +2.2 | +2.9 | +2.0 | +3.1 | +0.2 | +2.2 |
| 99.8 | -0.5 | -0.2 | -0.5 | -0.2 | -0.5 | 0.0 |

Altitude = 20,000 feet; Pressure = 349 Torr

| | | | | | | |
|---|---|---|---|---|---|---|
| 20.8 | +1.5 | +1.5 | +1.7 | +2.7 | +2.2 | +2.7 |
| 50.9 | -2.1 | -2.3 | -0.3 | -0.6 | -1.2 | -0.7 |
| 79.6 | -1.0 | -1.4 | -0.7 | -0.4 | -1.5 | +0.3 |
| 94.0 | +1.0 | +2.0 | +1.3 | +2.3 | -0.5 | +2.2 |
| 99.8 | -0.6 | -0.1 | -0.5 | -0.2 | -0.5 | -0.2 |

Altitude = 30,000 feet; Pressure = 226 Torr

| | | | | | | |
|---|---|---|---|---|---|---|
| 20.8 | +0.9 | +0.3 | +1.4 | +1.8 | +1.0 | +1.4 |
| 50.9 | -2.9 | -3.6 | -2.4 | -2.1 | -1.6 | -1.8 |
| 79.6 | -1.3 | -2.0 | -1.7 | -0.5 | -1.2 | -1.0 |
| 94.0 | +1.2 | +2.2 | +2.0 | +2.3 | -0.3 | +0.7 |
| 99.8 | -0.5 | -0.2 | -0.5 | -0.2 | -1.2 | -0.2 |

Altitude = 40,000 feet; Pressure = 141 Torr

| | | | | | | |
|---|---|---|---|---|---|---|
| 20.8 | +0.3 | -0.2 | +1.0 | +1.1 | +0.6 | +2.8 |
| 50.9 | -3.5 | -4.0 | -3.4 | -2.6 | -2.0 | 0.0 |
| 79.6 | -2.0 | -2.0 | -2.0 | -1.3 | -1.2 | +0.9 |
| 94.0 | +1.0 | +1.3 | 0.0 | +2.4 | -0.5 | +3.3 |
| 99.8 | -1.0 | -0.8 | -1.2 | -0.1 | -0.7 | -0.2 |

Equations 2 and 3 would probably fit data collected over a wider temperature range. However, the values of the constants would change. The temperature range of 288-308K was selected here simply for convenience. The entire operating temperature range of the apparatus was not investigated in this study.

The permeable membrane module used in this work was acquired under USAFSAM contract F33615-79-C-0609 with Airesearch Manufacturing Company, Torrance, California. The objective of the Airesearch contract was to evaluate the feasibility of generating oxygen onboard military aircraft by using membrane permeation enrichment of ambient air. Airesearch procured the hollow fiber membrane module from Dow Chemical Company, Walnut Creek, California. The results of the contract were published in USAFSAM-TR-80-24 titled "Aircraft Oxygen Generation by Membrane Permeation," November 1980.

Although the permeable membrane module used in the invention is the same module used in the Airesearch contract, the system configuration, function, and operating parameters differ significantly. The function of the module during the Airesearch contract was as an oxygen generator. In this work the function of the module was as an oxygen analyzer. The system configurations also differ greatly (compare Figures 2, 3, and 18 of SAM-TR-80-24 with Figure 1 of this work). In addition, the operating parameters, such as, inlet pressure, exhaust flow, and permeant flow differ markedly.

Although the Airesearch membrane module functioned adequately for this work, it would not be considered the optimum module for this invention because it is too bulky and does not contain a state-of-the-art hollow fiber membrane. This module was employed in this study because it was readily available and contained a permeable membrane with selectivity for oxygen. A state-of-the-art membrane module specifically designed to function as a oxygen analyzer would be smaller in size, require less inlet gas, and contain a permeable membrane with greater selectivity for oxygen. This greater selectivity would increase the shell-side flow and improve the overall accuracy of the apparatus.

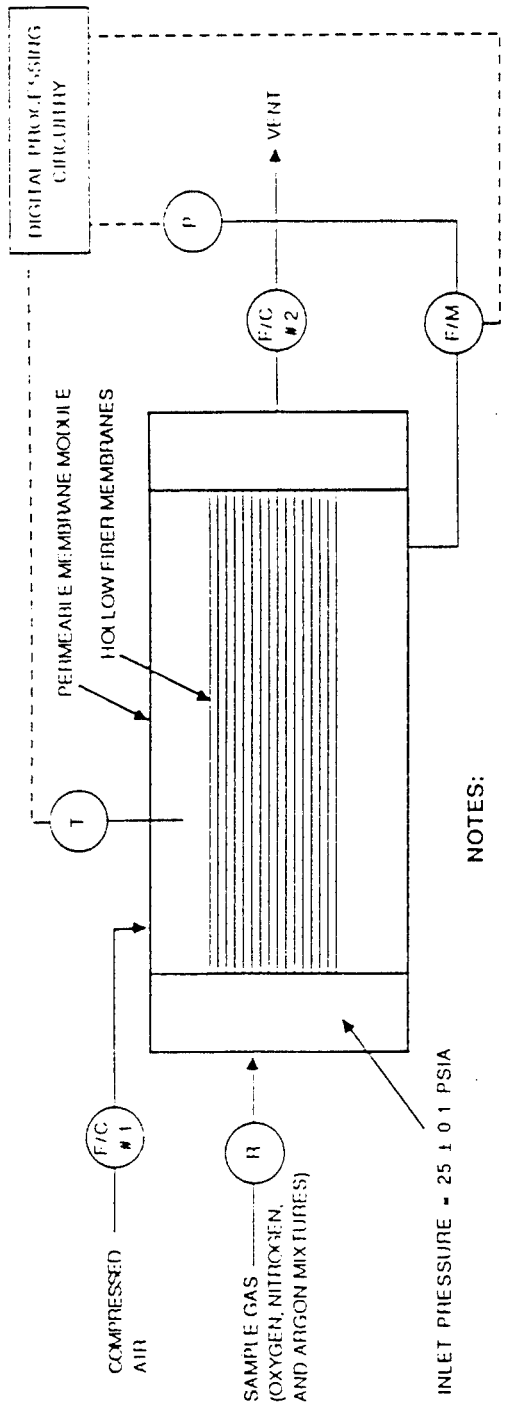
Figure 1. Schematic Diagram of the Apparatus for Oxygen Concentration Analysis.

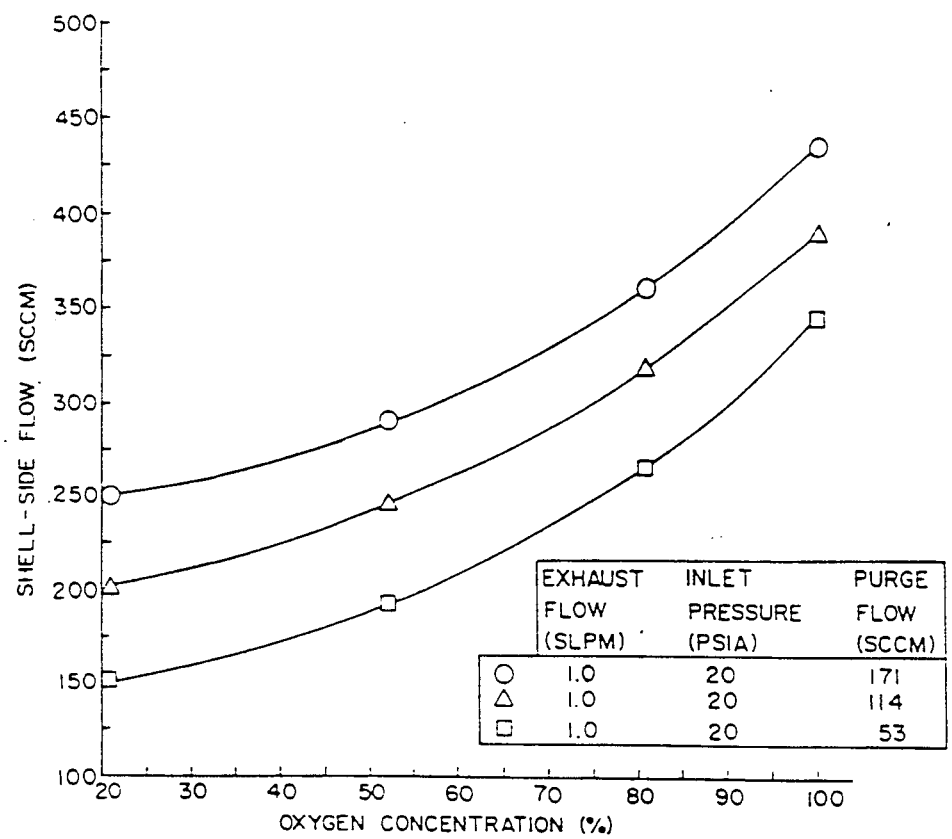
Figure 2. Data Taken on 6    198 .
(Vent pressure = 746 Torr; Ambient temperature = 297K)
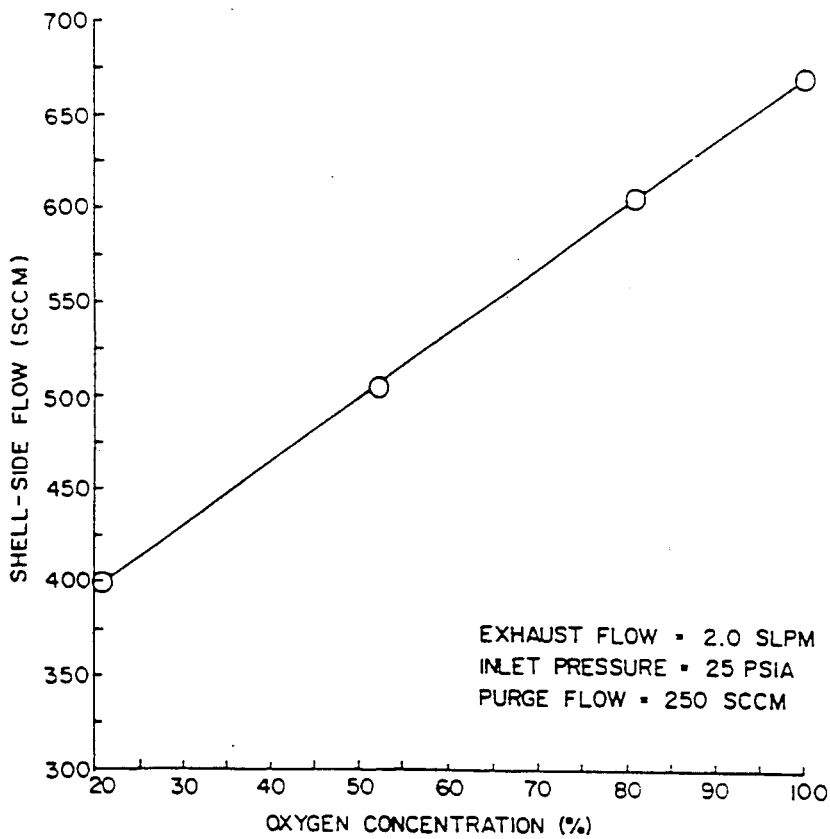
Figure 3. Data Taken on 13    198 .
(Vent pressure = 746 Torr; Ambient temperature = 297K)

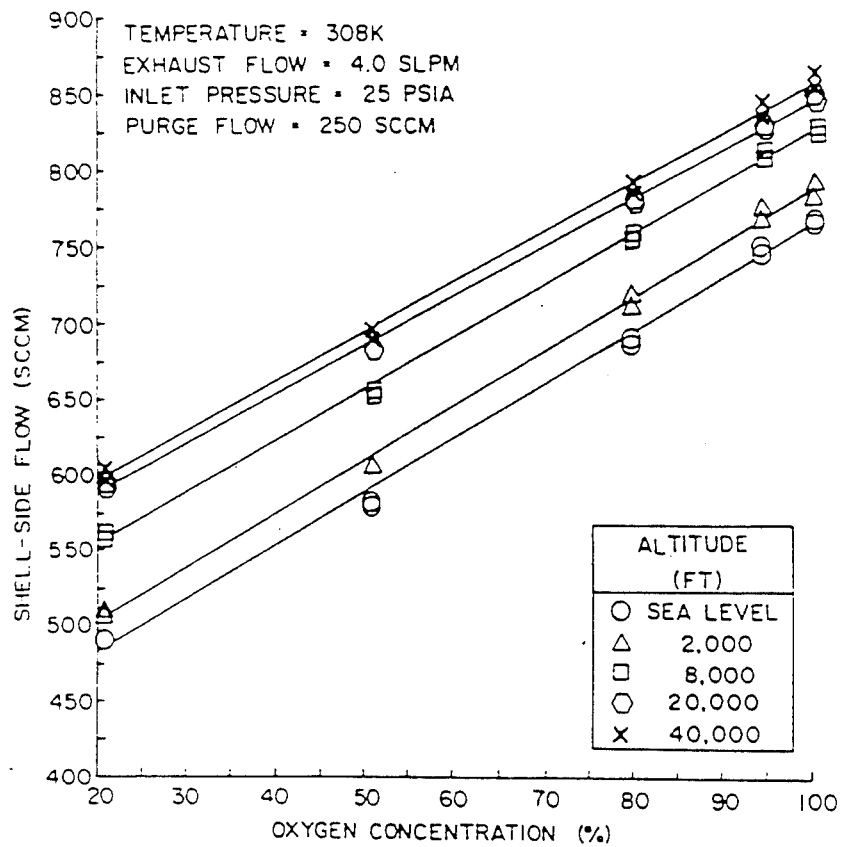
Figure 4. Data Taken at an Ambient Temperature of 308K.
(Runs 1 and 2 shown)
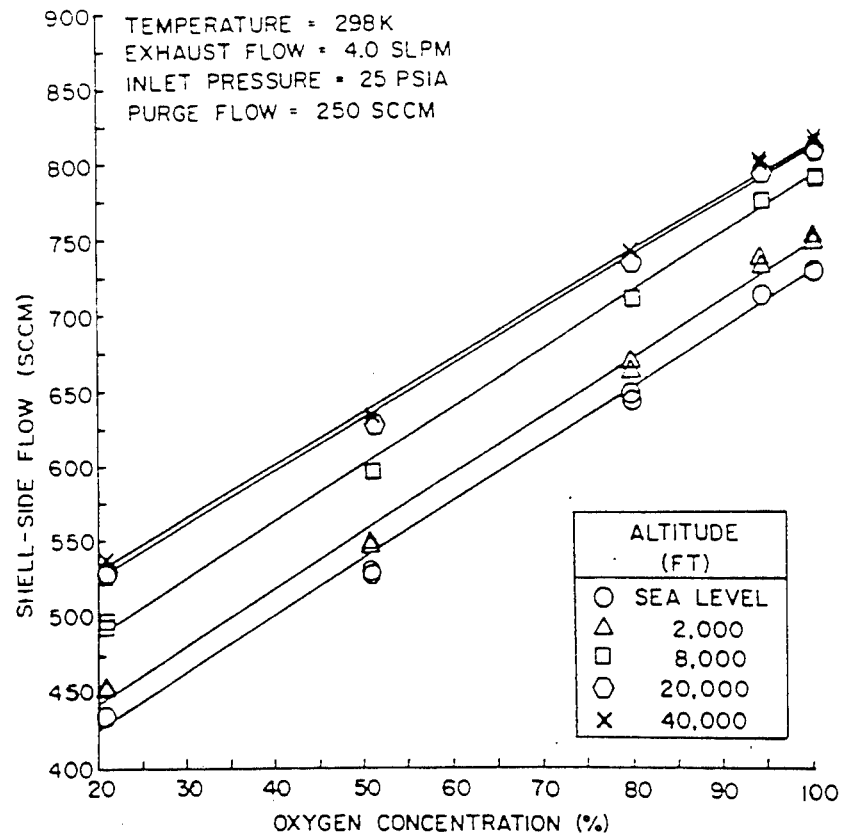
Figure 5. Data Taken at an Ambient Temperature of 298K.
(Runs 1 and 2 shown)

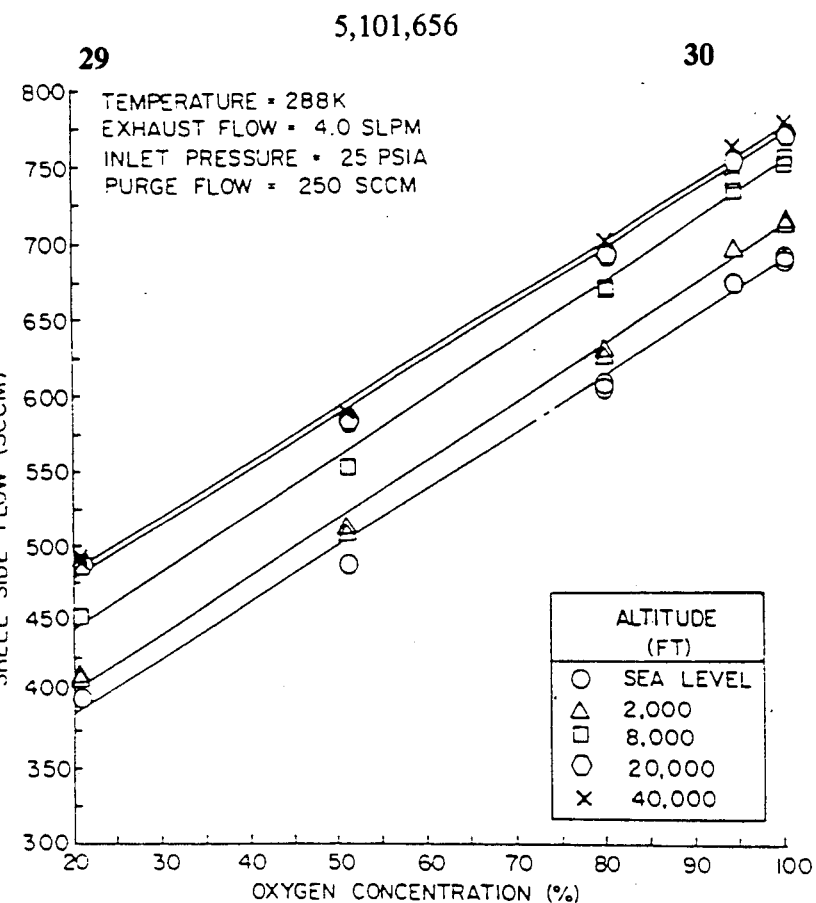
Figure 6. Data Taken at an Ambient Temperature of 288K.
(Runs 1 and 2 shown)
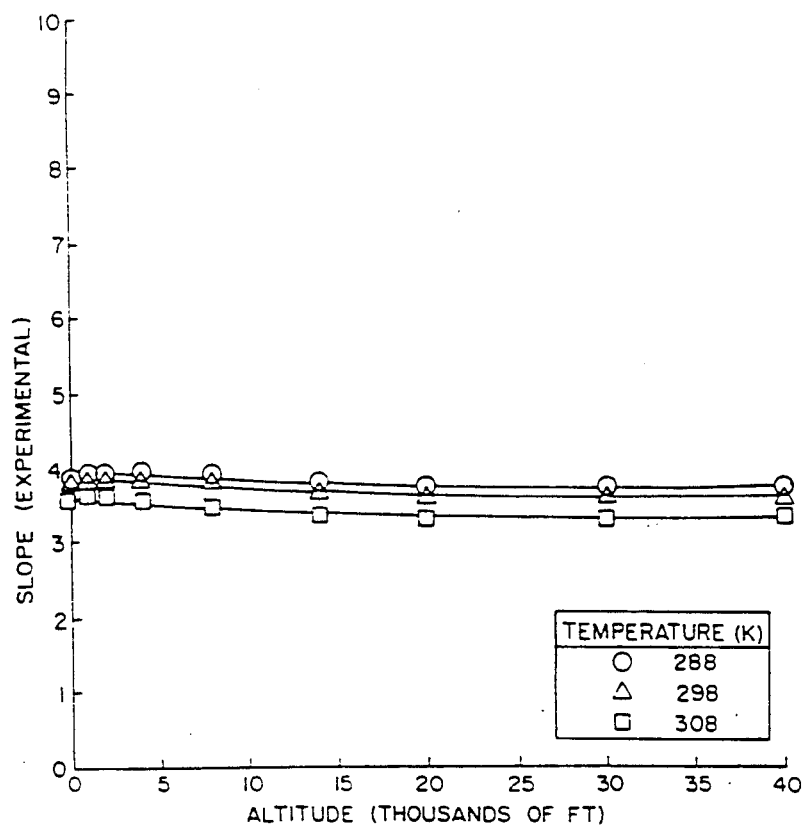
Figure 7. Experimental Slopes for the Apparatus Fit to Eqn 2.

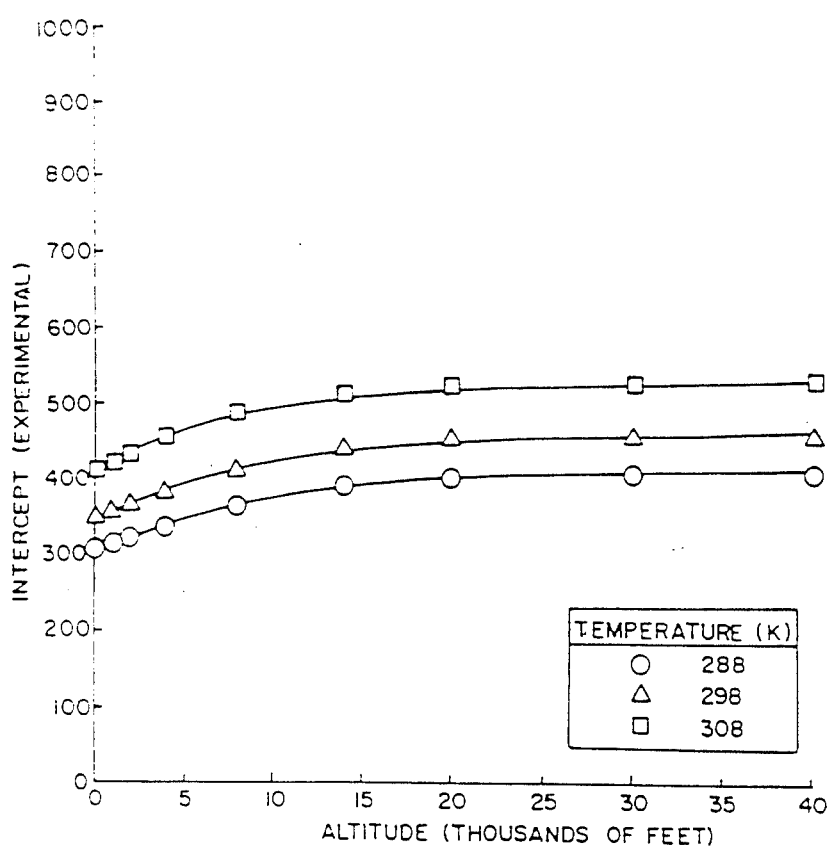
Figure d. Experimental Intercepts for the Apparatus Fit to Eqn 3.

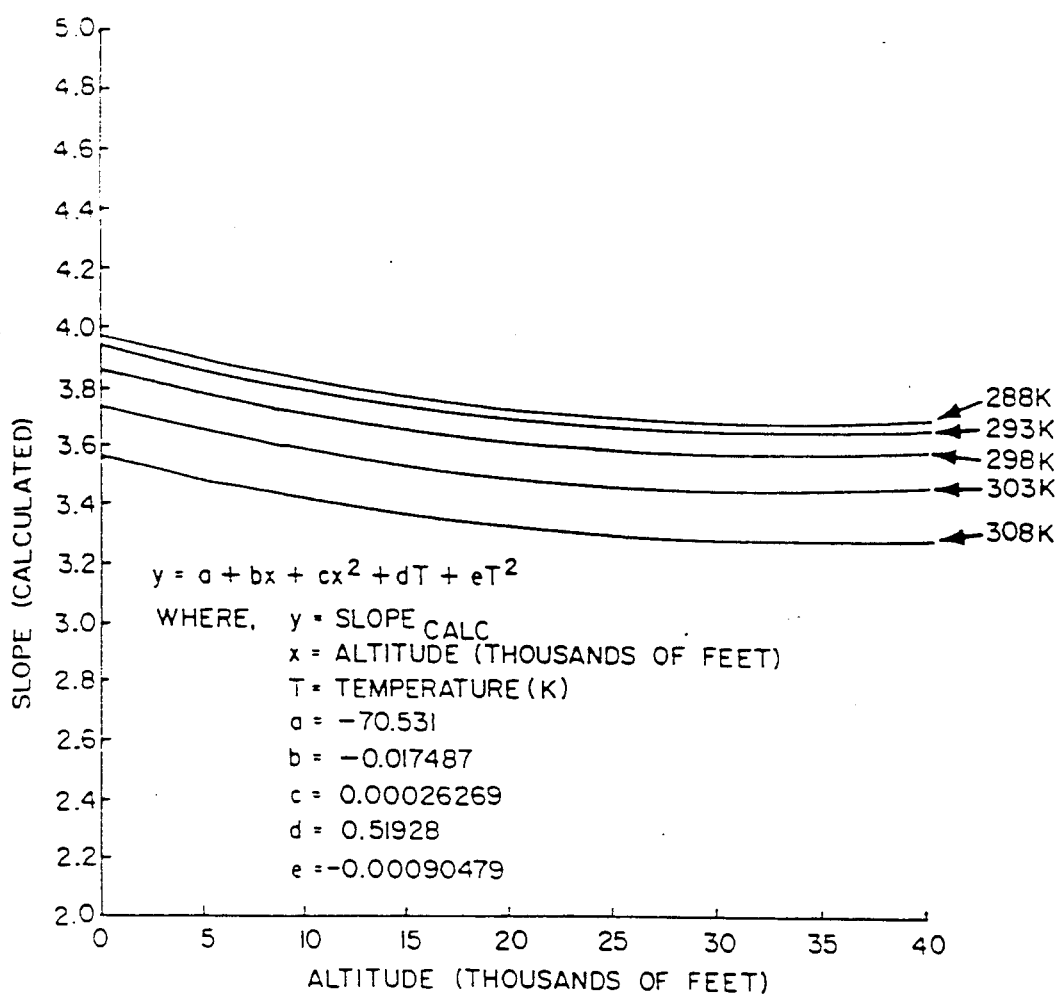
Figure 9. Calculated Slopes from Eqn 2.

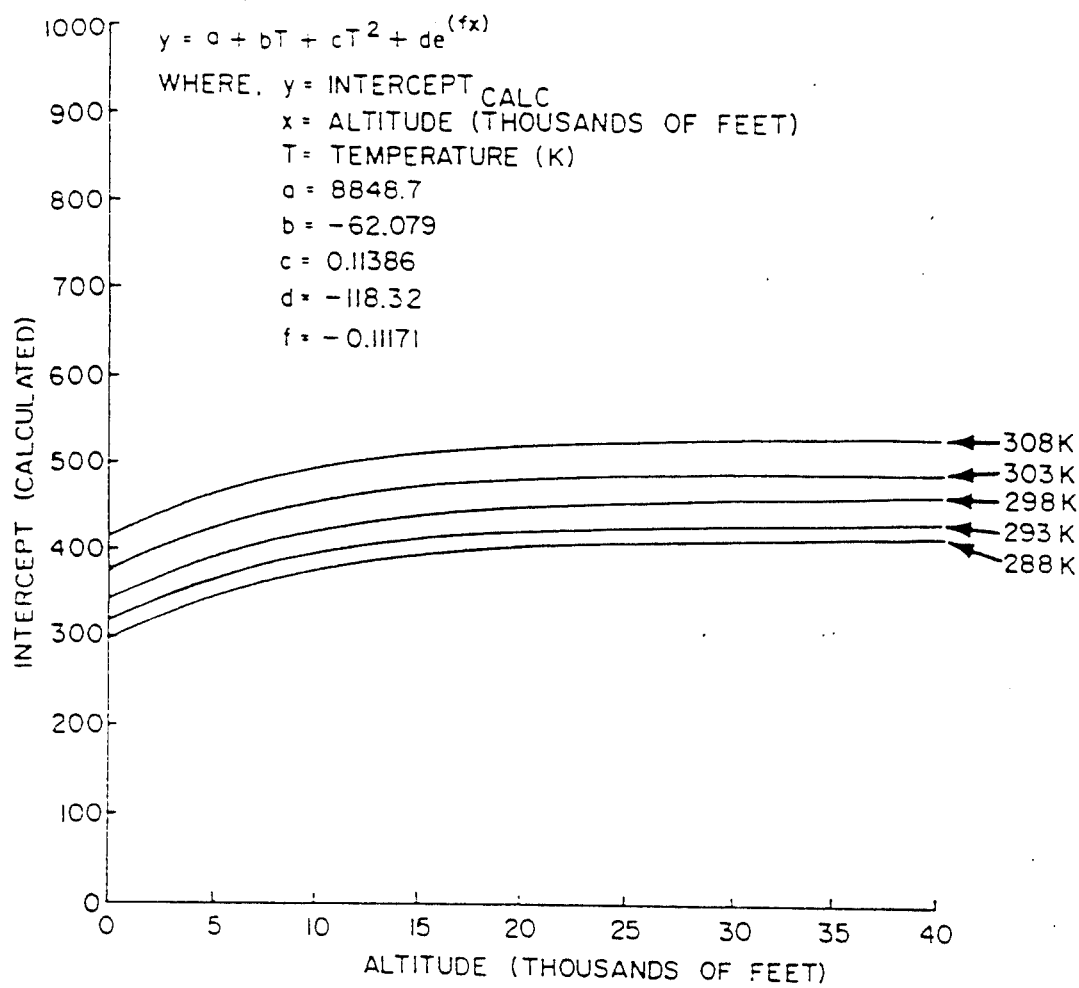
Figure 10. Calculated Intercepts from Eqn 3.

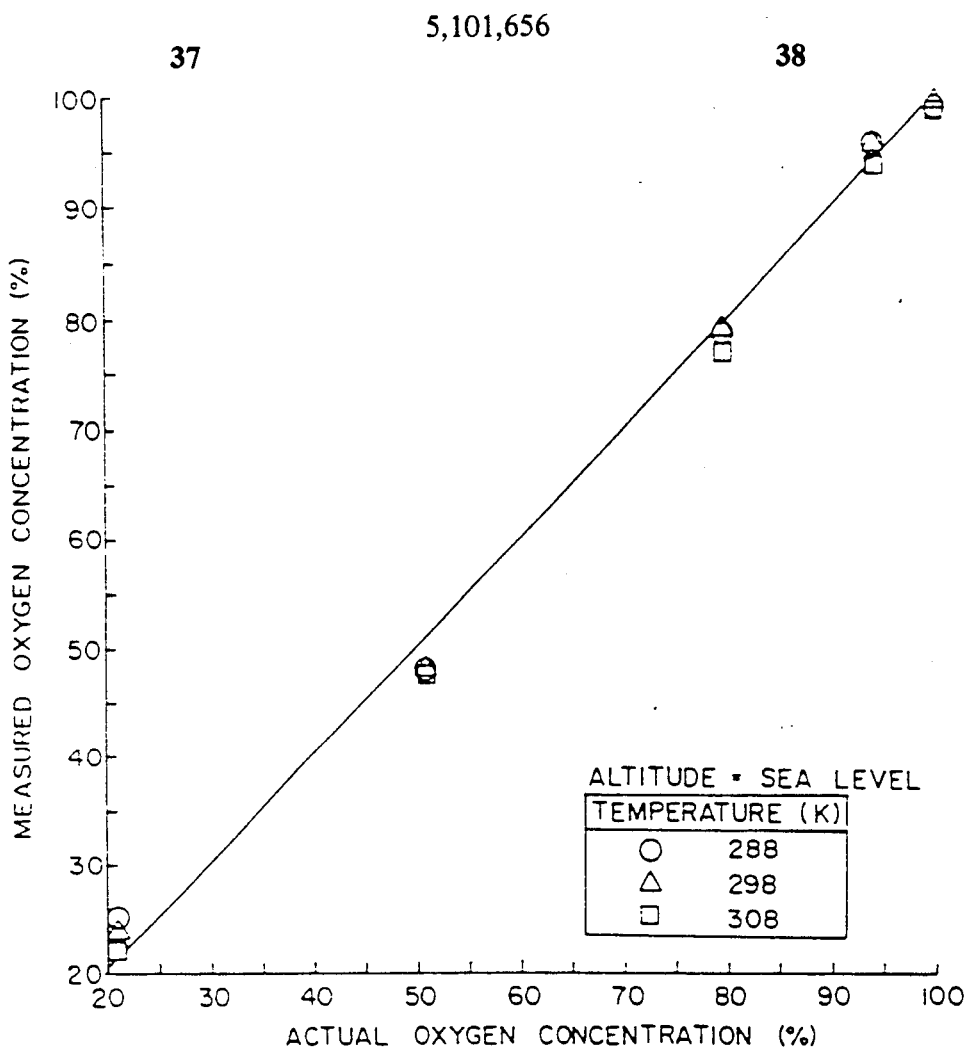
Figure 11. Actual versus Measured Oxygen Concentrations at Sea Level.

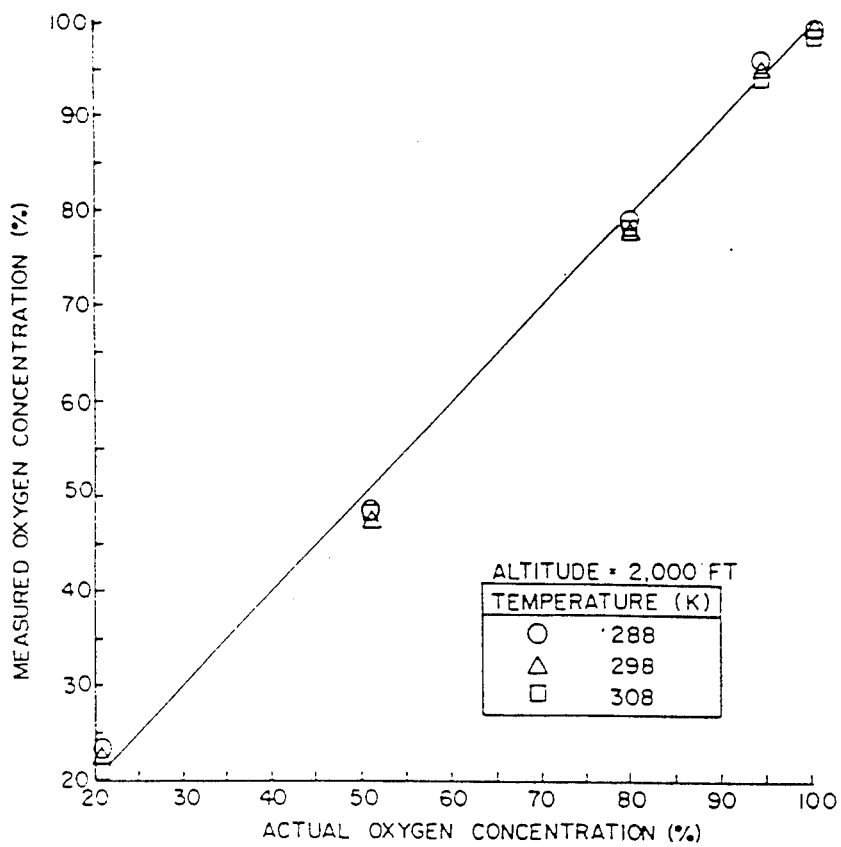
Figure 12. Actual versus Measured Oxygen Concentrations at an Altitude of 2,000 feet.
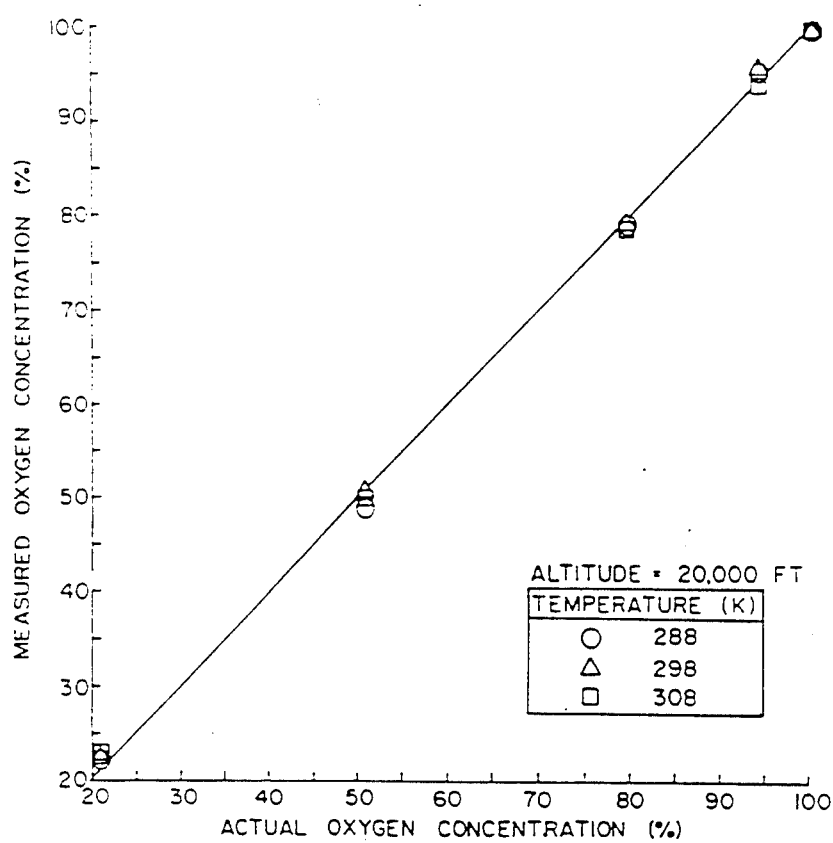
Figure 14. Actual versus Measured Oxygen Concentrations at an Altitude of 20,000 feet.

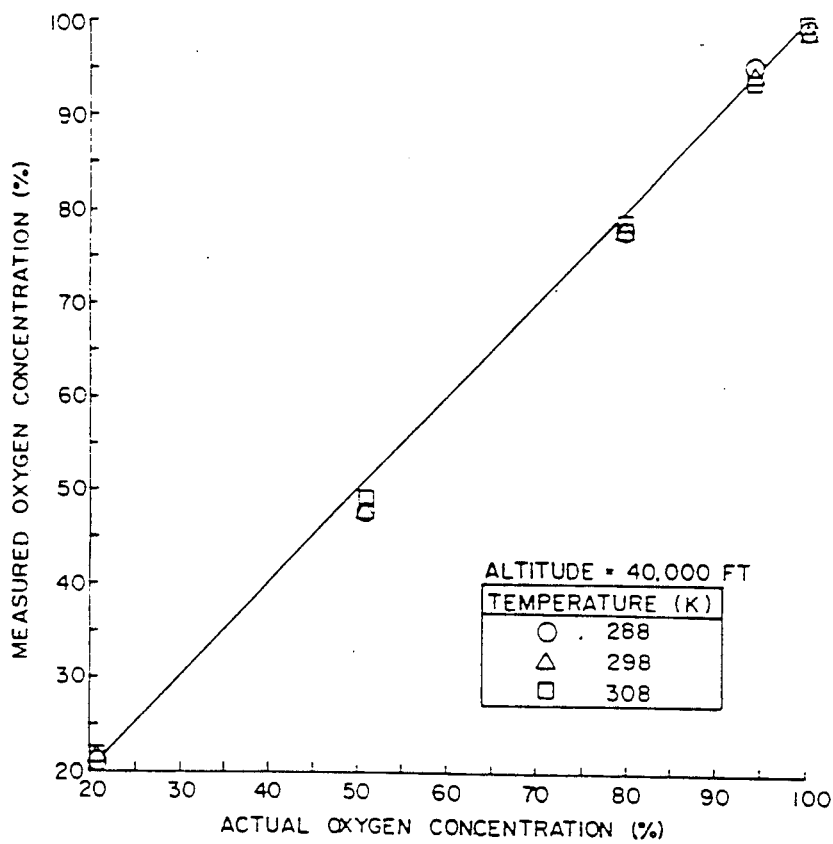
Figure 1b. Actual versus Measured Oxygen Concentrations at an Altitude of 40,000 feet.
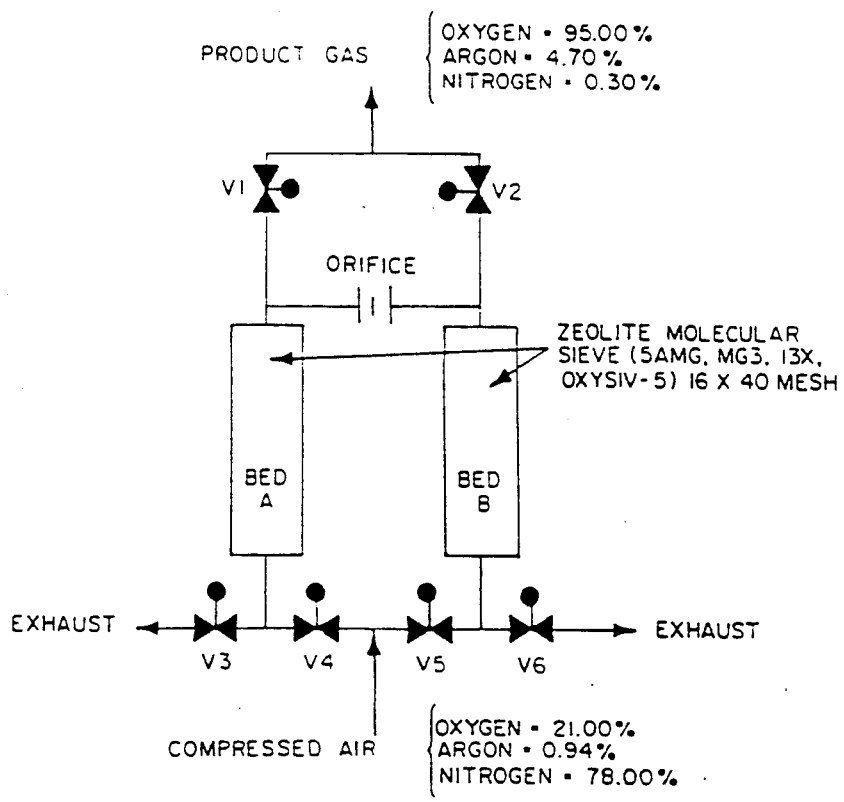
Figure 1o. Schematic of a Simple Two-Bed Molecular Sieve Oxygen Concentrator.

The concentrator functions by repeating steps of pressurization and depressurization. In FIG. 16 the cycle begins by the simultaneous opening of valves V1, V4, and V6. Valves V2, V3, and V5 remain closed. During this half-cycle bed A is pressurized with air and nitrogen is preferentially adsorbed resulting in the production of a concentrated oxygen stream at the bed outlet. During the second half-cycle valves V1, V4, and V6 close and valves V2, V3, and V5 open. In this half-cycle bed A desorbs the nitrogen to the ambient surrounding while bed B is pressured. An orifice connecting the outlet end of both beds allows a portion of the product gas to purge the depressurized bed. This purge improves the efficiency of the separation by sweeping the nitrogen gas out of the bed void volume. An adsorption bed completes one cycle of operation after passing through a pressurization and depressurization step. Generally, the duration of one cycle is 10 to 30 sec. The average oxygen and argon concentration of the product varies between 21-95% and 1-5% respectively, depending on several operating parameters, such as, inlet pressure, product flow, ambient temperature, and the activity or adsorption capacity of the molecular sieve.

What is claimed is:

1. A method for measuring the oxygen concentration of a gas mixture composed primarily of oxygen, nitrogen, and argon, using a membrane module having hollow fiber permeable membranes with a tube side and a shell side; in which the oxygen concentration is determined by measurement of shell side flow through the the membrane module; comprising:

passing a sample of said gas mixture as a stream through a pressure regulator and the tube-side of the membrane module, and thence via a vent flow controller to a vent as exhaust flow, the pressure regulator being used to maintain the module inlet pressure constant at a predetermined value, the vent flow controller being adjusted to permit sample gas to vent from the module at a given rate;

using a small portion of the flow which permeates through the membranes and enters the shell of the module as permeant gas for the measurement of the oxygen concentration of the gas mixture;

providing an air purge flow via an air flow controller at a given rate into the shell side of the membrane module, so that this flow combines with the permeant flow and serves to lower the concentration of oxygen near the outer surface of the membrane, with shell side flow exiting at the opposite end of the module as the incoming purge flow;

measuring the amount of shell side flow by a flowmeter, the shell side flow from the flowmeter being combined with the exhaust flow at the vent;

at intervals, using signals from the flowmeter along with measurements of module temperature and vent pressure to calculate the oxygen concentration of the sample of the gas mixture.

2. A method for measuring the oxygen concentration of a gas mixture composed primarily of oxygen, nitrogen, and argon, using a membrane module having hollow fiber permeable membranes with a tube side and a shell side; in which the oxygen concentration is determined by measurement of shell side flow through the the membrane module; comprising:

passing a sample of said gas mixture as a stream through a pressure regulator and the tube side of the membrane module, and thence via a vent flow controller to a vent as exhaust flow, the pressure regulator being used to maintain the module inlet pressure constant at 25±0.1 PSIA, the vent flow controller being adjusted to permit sample gas to vent from the module at a rate of 4.0 SLPM;

using a small portion of the flow which permeates through the membranes and enters the shell of the module as permeant gas for the measurement of the oxygen concentration of the gas mixture;

providing an air purge flow via an air flow controller at a rate of 250 SCCM into the shell side of the membrane module at an air pressure at an inlet to the air flow controller of approximately 35 PSIA, so that this flow combines with the permeant flow and serves to lower the concentration of oxygen near the outer surface of the membrane, with shell side flow exiting at the opposite end of the module as the incoming purge flow;

measuring the amount of shell side flow by a flowmeter, the shell side flow from the flowmeter being combined with the exhaust flow at the vent, a 0 to 5 VDC signal from the flowmeter representing a flow of 0 to 1000 SCCM;

each second, signals from the flowmeter, a temperature sensing device, and a pressure sensing device P being inputted to digital processing circuitry, using the digital processing circuitry to perform the following calculations:

a. converting the analog 0-5 VDC signal from the flowmeter to a value, y, between 0 and 1000 SCCM representing the shell side flow.

b. converting the analog signal from the temperature sensing device to a value, T, representing temperature in degrees Kelvin;

c. converting the analog signal from the pressure sensing device to a value, A, in units of Kft (thousands of feet) representing equivalent altitude;

d. determining the slope of the apparatus operating line at the specific altitude and temperature by the equation $$S = a + bA + cA^2 + dT + eT^2$$

where,
S = slope of the operating line
A = altitude in thousands of feet (Kft)
T = temperature (K.)
the constants for an operating temperature range of 288 to 308 K. and altitude range of 0 to 40Kft being:
a = −70.531
b = −0.017487
c = 0.00026269
d = 0.51928
e = −0.00090479 e. determining the intercept of the apparatus operating line by the equation $$I = a + bT + cT^2 + d\, e^{(f/a)}$$

where,
I = intercept of the operating line
A = altitude in thousands of feet (Kft)
T = temperature (K.)
constants for the temperature range of 288 to 308 K. and altitude range of 0 to 40Kft being:
a = 8848.7
b = −62.079
c = 0.11386 d = −118.32
e = 2.718282
f = −0.11171 f. calculating the oxygen concentration of the sample of the gas mixture by the equation $$x = \frac{y - I}{S} \quad (20.8 \leq x \leq 99.8)$$

where,
x = oxygen concentration (%)
y = shell side flow (SCCM)
S = slope (from above)
I = intercept (from above).

3. Apparatus for measuring the oxygen concentration of a sample of a gas mixture composed primarily of oxygen, nitrogen and argon; wherein said apparatus comprises a membrane module having hollow fiber permeable membranes with a tube side and a shell side;
 a source of compressed gas for said sample coupled via a gas regulator to the tube side at a first end of the membrane module, the purpose of the gas regulator being to maintain the module inlet pressure at a given constant value, so that the sample will flow through the tube side of the membrane module and a small portion of the flow will permeate through the membranes and enter the shell of the module as permeant gas;
 purge means comprising a first flow controller coupling a source of compressed air to the shell side at the first end of the membrane module, so that the compressed air will flow at a given rate into the shell side of the membrane module and will combine with the permeant flow and serve to lower concentration of oxygen near the outer surface of the membrane;
 a second flow controller coupled from a second end of the membrane module at the tube side to a vent for exhaust flow, the second flow controller being adjusted to permit sample gas to vent from the module at a given rate;
 a flowmeter coupled from the second end of the membrane module at the shell side to the vent for measuring the amount of shell side flow;
 a signal processing circuit, an electrical connection from the flowmeter to the signal processing means;
 a temperature sensing device connected to the membrane module, with an electrical connection to the signal processing means, for providing a temperature value; means with an electrical connection to the signal processing circuit for indicating a pressure value which is a function of the pressure at the vent;
 wherein the signal processing circuit includes means for calculating the oxygen concentration of said sample of the gas mixture, as a function of signals from the flowmeter, said temperature value, said pressure value, and predetermined equations and constants stored in the signal processing circuit.

* * * * *

UNITED STATES PATENT AND TRADEMARK OFFICE
CERTIFICATE OF CORRECTION

PATENT NO. : 5,101,656

DATED : April 14, 1992

INVENTOR(S) : George W. Miller

It is certified that error appears in the above-identified patent and that said Letters Patent is hereby corrected as shown below:

Column 2, line 48, a period should follow "sensor".

Column 8, line 7, (Eq 2), "$e^{(fa)}$" should be --$e^{(fA)}$--.

Column 11, line 12 (Appendix), the following text should be inserted:

-- Data collected on 13    8 are shown in Table 2 and Figure 3. Based on this data, it was determined adjustment of the operating peramters (exhaust flow, inlet pressure, and purge flow) can result in a nearly linear response.

Table 2. Data Collected on    8 .
(Apparatus vented to ambient pressure of 746 Torr; Ambient temperature = 297K)

| Sample Gas Oxygen Conc. (%) | Exhaust Flow (SLPM) | Inlet Pressure (PSIA) | Purge Flow (SCCM) | Shell-side Flow (SCCM) |
|---|---|---|---|---|
| 20.8 | 2.0 | 25 | 250 | 400 |
| 52.2 | 2.0 | 25 | 250 | 505 |
| 80.7 | 2.0 | 25 | 250 | 605 |
| 99.5 | 2.0 | 25 | 250 | 670 |

Notes (see Figure 1):
Purge flow is controlled by flow controller F/C #1.
Exhaust flow is controlled by flow controller F/C #2.
Inlet pressure is controlled by gas regulator R.
Shell-side flow is measured by flow meter F/M.
The remainder of the inlet gas was nitrogen.

UNITED STATES PATENT AND TRADEMARK OFFICE
CERTIFICATE OF CORRECTION

PATENT NO. : 5,101,656

DATED : April 14, 1992

INVENTOR(S) : George W. Miller

It is certified that error appears in the above-identified patent and that said Letters Patent is hereby corrected as shown below:

During          through          198   the apparatus was operated at the conditions given below, a. Exhaust Flow = 4.0 SLPM
    b. Inlet Pressure = 25 PSIA
    c. Air Purge Flow = 250 SACCM Data were collected at several simulated altitudes (or vent pressures) and temperatures (288, 298, and 308K) using the operating conditions given above (Table 4 and Figures 4-6). During these experiments the temperature of the apparatus was maintained constant by an ethylene glycol-water bath. The simulated altitudes were achieved by connecting the apparatus vent to a plenum maintained at a lowered pressure. The exhaust flow was set at 4.0 SLPM to improve the response time of the apparatus. The sample gas mixtures used in these tests are listed in Table 3. Gas mixtures 1 through 4 were selected because they simulate actual gas mixtures produced by a molecular sieve oxygen concentrator.

Table 3. Gas Mixtures Used to Test the Apparatus --.

Column 17, last line (Appendix), the line should read:
    --for Run 1 at sea level, 2,000, 8,000, 20,000, and 40,000
    feet are --.

UNITED STATES PATENT AND TRADEMARK OFFICE
CERTIFICATE OF CORRECTION

PATENT NO. :     5,101,656

DATED     :     April 14, 1992

INVENTOR(S) :   George W. Miller

It is certified that error appears in the above-identified patent and that said Letters Patent is hereby corrected as shown below:

Column 39 (Appendix Figures), the following Figure 13 should appear:

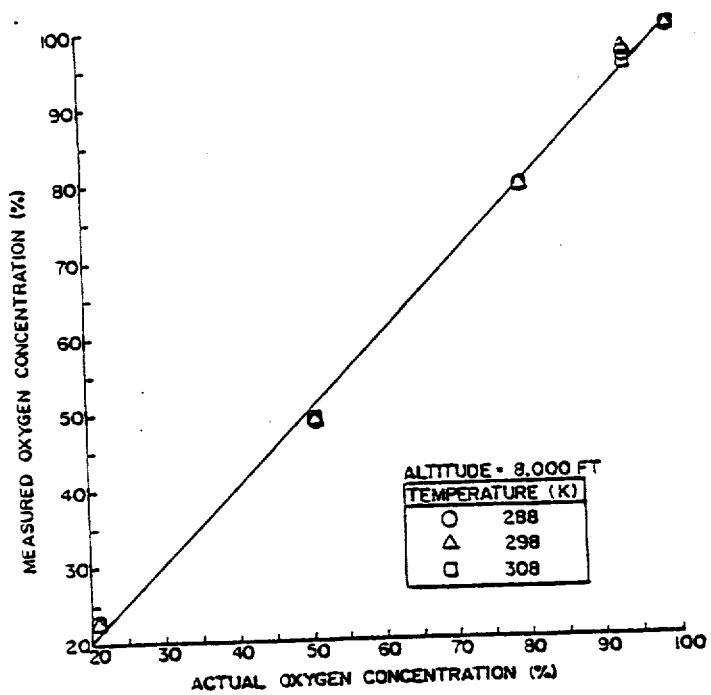

Figure 13. Actual versus Measured Oxygen Concentrations at an Altitude of 8,000 feet.

UNITED STATES PATENT AND TRADEMARK OFFICE
CERTIFICATE OF CORRECTION

PATENT NO. : 5,101,656
DATED : April 14, 1992
INVENTOR(S) : George W. Miller

It is certified that error appears in the above-identified patent and that said Letters Patent is hereby corrected as shown below:

Column 43, line 30, --the-- should follow "of".
Column 43, line 56, --the-- should follow "of".
Column 44, line 31, the period should be a semicolon.
Column 44, line 59, "$e^{(fa)}$" should be --$e^{(fA)}$--.

Signed and Sealed this

Eighteenth Day of October, 1994

Attest:

BRUCE LEHMAN

*Attesting Officer*   *Commissioner of Patents and Trademarks*